(12) United States Patent
Haun et al.

(10) Patent No.: US 12,036,550 B2
(45) Date of Patent: *Jul. 16, 2024

(54) MICROFLUIDIC DEVICE FOR THE DIGESTION OF TISSUES INTO CELLULAR SUSPENSIONS

(71) Applicant: THE REGENTS OF THE UNIVERSITY OF CALIFORNIA, Oakland, CA (US)

(72) Inventors: Jered Haun, Irvine, CA (US); Xiaolong Qiu, Chula Vista, CA (US); Elliot Hui, Arcadia, CA (US); Amrith Karunaratne, Carson, CA (US); Erik Werner, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 753 days.

This patent is subject to a terminal disclaimer.

(21) Appl. No.: 17/180,711

(22) Filed: Feb. 19, 2021

(65) Prior Publication Data
US 2021/0197191 A1 Jul. 1, 2021

Related U.S. Application Data

(63) Continuation-in-part of application No. 16/115,434, filed on Aug. 28, 2018, now Pat. No. 10,926,257.
(Continued)

(51) Int. Cl.
*B01L 3/00* (2006.01)

(52) U.S. Cl.
CPC ..... *B01L 3/50273* (2013.01); *B01L 2200/027* (2013.01); *B01L 2200/0647* (2013.01); *B01L 2300/042* (2013.01); *B01L 2300/0816* (2013.01)

(58) Field of Classification Search
CPC ........... B01L 3/50273; B01L 3/502753; B01L 3/502746; B01L 2200/027;
(Continued)

(56) References Cited

U.S. PATENT DOCUMENTS 9,580,678 B2   2/2017 Haun et al.
10,926,257 B2 * 2/2021 Haun ................ B01L 3/502715
(Continued)

FOREIGN PATENT DOCUMENTS

WO    2012/139209    10/2012

OTHER PUBLICATIONS

PCT International Search Report for PCT/US2022/016855, Applicant: The Regents of the University of California, Form PCT/ISA/210 and 220, dated Jun. 30, 2022 (5 pages).
(Continued)

*Primary Examiner* — Michael L Hobbs
(74) *Attorney, Agent, or Firm* — VISTA IP LAW GROUP LLP

(57) ABSTRACT

A microfluidic device uses hydrodynamic shear forces on a sample to improve the speed and efficiency of tissue digestion is disclosed. The microfluidic channels are designed to apply hydrodynamic shear forces at discrete locations on tissue specimens up to 1 cm in length and 1 mm in diameter, thereby accelerating digestion through hydrodynamic shear forces and improved enzyme-tissue contact. The microfluidic digestion device can eliminate or reduce the need to mince tissue samples with a scalpel, while reducing sample processing time and preserving cell viability. Another advantage is that downstream microfluidic operations could be integrated to enable advanced cell processing and analysis capabilities. The device may be used in research and clinical settings to promote single cell-based analysis technologies, as well as to isolate primary, progenitor, and stem
(Continued)

cells for use in the fields of tissue engineering and regenerative medicine.

22 Claims, 20 Drawing Sheets

Related U.S. Application Data

(60) Provisional application No. 62/551,172, filed on Aug. 28, 2017.

(58) Field of Classification Search
CPC ....... B01L 2200/0647; B01L 2300/042; B01L 2300/0816; B01L 2300/0681; B01L 2400/0487; B01L 2400/086; C12M 45/02; C12M 45/09; G01N 1/4044; G01N 15/1484; G01N 15/1459; G01N 2015/1006
See application file for complete search history.

(56) References Cited

U.S. PATENT DOCUMENTS

| | | | |
|---|---|---|---|
| 2009/0098541 A1 | 4/2009 | Southern | |
| 2013/0152456 A1 | 6/2013 | Powell | |
| 2013/0295598 A1* | 11/2013 | Marx | C12M 21/08 435/303.1 |
| 2014/0057311 A1 | 2/2014 | Kamm et al. | |
| 2014/0377866 A1 | 12/2014 | Haun et al. | |
| 2015/0377861 A1 | 12/2015 | Pant et al. | |
| 2016/0313306 A1 | 10/2016 | Ingber et al. | |
| 2017/0131187 A1 | 5/2017 | Haun et al. | |
| 2019/0062684 A1 | 2/2019 | Neumann et al. | |
| 2019/0070605 A1 | 3/2019 | Haun et al. | |
| 2019/0106664 A1 | 4/2019 | Hung et al. | |

OTHER PUBLICATIONS

PCT Written Opinion of the International Search Authority for PCT/US2022/016855, Applicant: The Regents of the University of California, Form PCT/ISA/237, dated Jun. 30, 2022 (7 pages).

Hattersley, Samantha M. et al., Development of a microfluidic device for the maintenance and interrogation of viable issue biopsies, Lab Chip, 8(11), pp. 1842-1846 (2008).

Lin, Ching-Hui et al., Separation of Heterogeneous Neural Cells in Neurospheres using Microfluidic Chip, Anal Chem, 85, 11920-8 (2013).

Wallman, Lars et al., Biogrid—a microfluidic device for large-scale enzyme-free dissociation of stem cell aggregates, Lab Chip, 11(19), pp. 3241-3248 (2011).

Qui, Xiaolong et al., Microfluidic device for mechanical dissociation of cancer cell aggregates into single cells, Lab Chip. Jan. 7, 2015; 15(1):339-350. doi:10.1039/c41c01126k.

Kim, M. Y. et al., Microfabrication of High-Resolution Porous Membranes for Cell Culture, J. Memb. Sci. 452, 460-469 (2014).

MACS Miltenyi Biotec, gentleMACSTM Dissociator, The gentle way of automated tissue dissociation, gentlemacs.com, (2010) (2pages).

Bianchi, Francesca et al., A New Nonenzymatic Method and Device to Obtain a Fat Tissue Derivative Highly Enriched In Pericyte-Like Elements by Mild Mechanical Forces Human Lipoaspirates, Cell Transplantation, vol. 22, pp. 2063-2077, 2013.

Conde-Green, Alexandra et al., Effects of Centrifugation on Cell Composition and Viability of Aspirated Adipose Tissue Processed for Transplantation, Aesthetic Surgery Journal 30(2) 249-255 (2010).

Conde-Green, Alexandra et al., Infulence of decantation, washing and centrifugation on adipocyte and mesenchymal stem cell content of aspirated adipose tissue: A comparative stury, Journal of Plastic, Reconstructive & Aesthetic Surgery (2010) 63, 1375-1381.

Heneidi, Saleh et al., Awakened by Cellular Stress: Isolation and Characterization of a Novel Population of Pluripotent Stem Cells Derived from Human Adipose Tissue, PLOS ONE, www.plosone.org, Jun. 2013, vol. 8, Issue 6, e64752.

Banyard, Derk A. et al., Phenotypic Analysis of Stromal Vascular Fraction after Mechanical Shear Reveals Stress-Induced Progenitor Populations, Pastic and Reconstructive Surger, Aug. 2016, vol. 138, No. 2, Shear Stress Progenitor Morphogenesis, www.PRSJournal.com, 237e-247e.

Tonnard, Patrick et al., Nanofat Grafting: Basic Research and Clinical Applications, Plastic and Reconstructive Surgery, Oct. 2013, vol. 132, No. 4, Nanofat Grafting, www.PRSJournal.com, 2013.

PCT International Preliminary Report on Patentability (Chapter I of the Patent Cooperation Treaty) for PCT/US2022/016855, Applicant: The Regents of the University of California, Form PCT/IB/326 and 373, dated Aug. 31, 2023 (9 pages).

\* cited by examiner

MICROFLUIDIC DEVICE FOR THE DIGESTION OF TISSUES INTO CELLULAR SUSPENSIONS

RELATED APPLICATIONS

This Application is a continuation-in-part of U.S. patent application Ser. No. 16/115,434, filed on Aug. 28, 2018, now issued as U.S. Pat. No. 10,926,257, which also claims priority to U.S. Provisional Patent Application No. 62/551,172 filed on Aug. 28, 2017, which are hereby incorporated by reference in their entirety. Priority is claimed pursuant to 35 U.S.C. §§ 119, 120 and any other applicable statute.

STATEMENT REGARDING FEDERALLY SPONSORED RESEARCH AND DEVELOPMENT

This invention was made with Government support under Grant No. IIP-1362165, awarded by the National Science Foundation. The Government has certain rights in the invention.

TECHNICAL FIELD

The technical field generally relates to microfluidic devices that are used to digest tissue specimens or tissue samples into cellular suspensions.

BACKGROUND

The past decade has seen a rapid growth in interest to harvest single cells from tissues that has spanned across several biomedical research areas. This has been driven in part by the rise in use of single cell analysis techniques, such as flow cytometry, mass spectroscopy, and single cell sequencing, to identify and profile the diverse cell types typically found within tissues. For cancer, this has enabled assessment of tumor heterogeneity, metastatic potential, and the presence of rare cell types such as putative cancer stem cells. These insights obtained at the resolution of single cells are drastically changing the understanding of cancer, and in the future are poised to revolutionize clinical diagnostics and inform personalized patient care. In the field of tissue engineering, isolation of primary cells from tissues is critical for the creation of new constructs to replace damaged organs, such as skin, liver, heart, pancreas and kidney. Finally, a major goal of regenerative medicine is to isolate mesenchymal stem cells and progenitor cells from tissues to heal or otherwise replace diseased parts of the body. A common theme unifying all of these applications is that they require viable single cells that remain as representative of their original phenotypic state as possible. Thus, there is a critical need to develop new technologies that will make it possible to liberate single cells from tissues in a rapid, gentle, and thorough manner.

Microfluidic technologies have emerged as simple yet powerful methods for processing and manipulating cellular samples at the microscale. However, only a few microfluidic devices have been developed to work with cell aggregates and tissues. The microfluidic cell dissociation chip (µ-CDC) described by Lin et al. was designed to break down neurospheres under fluid flow using a micro-pillar array. See Lin et al., Separation of Heterogenous Neural Cells in Neurospheres using Microfluidic Chip, Anal Chem, 85, 11920-8 (2013). However, this device could only be used with aggregates that were less than 300 µm in diameter, and yet still suffered from clogging issues. Wallman et al. disclosed a Biogrid device that was designed to mechanically cut neurospheres using sharp silicon knife-edges placed across the device cross-section. See Wallman et al., Biogrid—a microfluidic device for large-scale enzyme-free dissociation of stem cell aggregates, Lab Chip, 11(19), pp. 3241-8 (2011). While more effective, mechanical cutting in this fashion was harsh and only resulted in smaller aggregates, not single cells. In previous work, a microfluidic device was disclosed that employed a network of branching channels to achieve highly efficient and rapid dissociation of cancer cell aggregates into viable single cells. See Qui et al., Microfluidic device for mechanical dissociation of cancer cell aggregates into single cells, Lab on a Chip, 15.1, 339-350 (2015). However, the inlet could not accommodate samples that were greater than 1 mm in size, requiring off-chip mincing and digestion of larger tissue specimens. While full scale tissues have been employed in a single microfluidic application, namely, the culture and enzymatic digestion of rat liver biopsies, this device has a number of limitations. See Hattersley et al., Development of a microfluidic device for the maintenance and interrogation of viable tissue biopsies, Lab Chip, 8(11), pp. 1842-6 (2008). For example, this device just provided a means to incubate tissues with enzymes, and suffered from extremely low cell yields, even after prolonged digestion times.

SUMMARY

In one embodiment, a microfluidic device for the processing of a tissue sample into cellular suspensions includes a substrate or chip having formed therein an inlet, an outlet, and a sample chamber dimensioned to hold the tissue sample. The sample chamber is fluidically coupled at one side to a plurality of upstream hydro-mincing microfluidic channels disposed in the substrate or chip. These upstream hydro-mincing microfluidic channels drive the fluid into discrete locations of the tissue in a jetting process, effectively mincing it through the application of hydrodynamic shear forces and improved enzyme penetration (contained in the fluid). The sample chamber is further fluidically coupled at another side of the sample chamber to a plurality of downstream sieve microfluidic channels disposed in the substrate or chip and further fluidically coupled to the outlet. The downstream sieve microfluidic channels act as a sieve that firmly holds the tissue in place while also allowing smaller aggregates and cells to exit the sample chamber.

In some embodiments, the microfluidic device may be coupled with downstream operations such as secondary microfluidic dissociation devices to better liberate single cells from small aggregates. Valves may also optionally be incorporated into or associated with the upstream hydro-mincing microfluidic channels to provide a high degree of shear forces on selected or targeted areas or regions of tissue. These valves can be turned on and off to cover the entire length of tissue in the chamber. In addition, cell sorting and analysis components may be added to create point-of-care platforms for cell-based diagnostics and therapies.

In another embodiment, a method of processing tissue using the microfluidic device includes placing the tissue within the sample chamber and then flowing a fluid containing a digestive enzyme into the inlet. The tissue that may be processed using the microfluidic device may include healthy or diseased tissue. For example, in one particular embodiment, the tissue that is processed by the device includes tumor tissue, although other tissue types are contemplated. Tissue obtained from different organs may also be treated. Examples include liver tissue, kidney tissue, pancreas tissue, spleen tissue, skin tissue, heart tissue, and the like. The fluid may be pumped into the microfluidic device using a pump. The cells or smaller aggregates of tissue may be collected from the outlet of the microfluidic device. In some embodiments, the collected output from the microfluidic device is recirculated back into the input of the microfluidic device.

In some embodiments, the tissue is loaded into the sample chamber by using a sample port. In some embodiments the sample is loaded by inserting a needle into the sample port and depositing the tissue in the sample chamber. In other embodiments, a plug, cap, or lid covers the sample chamber and can be removed/secured to the microfluidic device.

A microfluidic system for the processing of a tissue sample dimensioned within the range of 1 mm 3 to 50 mm$^3$ into cellular suspensions including a microfluidic device formed from a substrate or chip having formed therein an inlet, an outlet, and a sample chamber dimensioned to hold the tissue sample, the sample chamber fluidically coupled at a first side to a plurality of upstream hydro-mincing microfluidic channels disposed in the substrate or chip further fluidically coupled to the inlet and coupled at a second side of the sample chamber to a plurality of downstream sieve microfluidic channels disposed in the substrate or chip further fluidically coupled to the outlet; wherein both the width of the upstream hydro-mincing microfluidic and the width of the downstream sieve microfluidic channels are greater than 50 µm and are smaller than the smallest dimension of the tissue sample.

A method of processing tissue in a microfluidic device that is formed in a substrate or chip having formed therein an inlet, an outlet, and a sample chamber dimensioned to hold the tissue sample, the sample chamber fluidically coupled at one side to a plurality of upstream hydro-mincing microfluidic channels disposed in the substrate or chip and further fluidically coupled to the inlet and coupled at another side of the sample chamber to a plurality of downstream sieve microfluidic channels disposed in the substrate or chip and further fluidically coupled to the outlet. The method includes placing the tissue within the sample chamber and flowing a fluid containing a digestive enzyme into the inlet.

BRIEF DESCRIPTION OF THE DRAWINGS

The features and advantages of the present invention will become apparent from a consideration of the following detailed description presented in connection with the accompanying drawings in which.

DETAILED DESCRIPTION OF THE ILLUSTRATED EMBODIMENTS

Figure 1:
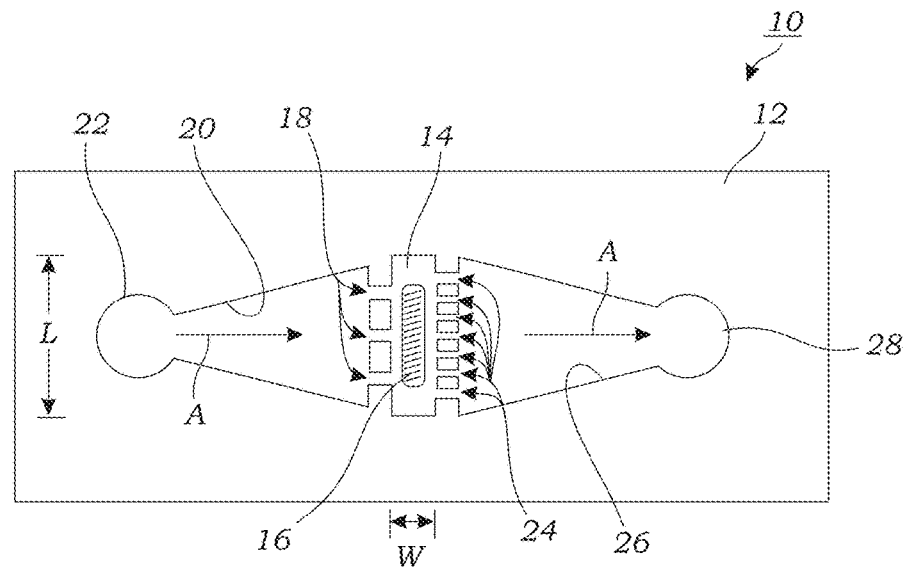
FIG. 1 illustrates a top view of one embodiment of a microfluidic device for the processing and digestion of tissue according to one embodiment.

FIG. 1 illustrates microfluidic device 10 for the processing and digestion of tissue according to one embodiment. In one particular embodiment, the microfluidic device 10 is designed to process tissue obtained from a mammalian subject (e.g., human). In particular, the microfluidic device 10 has particular applicability for the processing and digestion of tumor tissues, although other tissue types may be processed using the microfluidic device 10. The microfluidic device 10 is formed in a substrate or chip structure 12 which as explained herein may be formed using multiple layers that are assembled together to form the microfluidic device 10. The microfluidic device 10 includes three primary features that are defined or formed in the substrate or chip structure 12. These include a sample chamber 14 that holds a sample 16 in place while fluid containing proteolytic enzymes or other digestive agents is passed into the sample chamber 14 and onto the surface of the sample 16. The sample chamber 14 thus maintains the sample 16 in a generally fixed location in the substrate or chip structure 12. By having the sample 16 be retained in the sample chamber 14, this promotes sample mixing, enhances enzymatic activity, and as explained below applies hydrodynamic shear forces to mechanically dislodge cells and aggregates from the larger sample 16.

Figure 20:
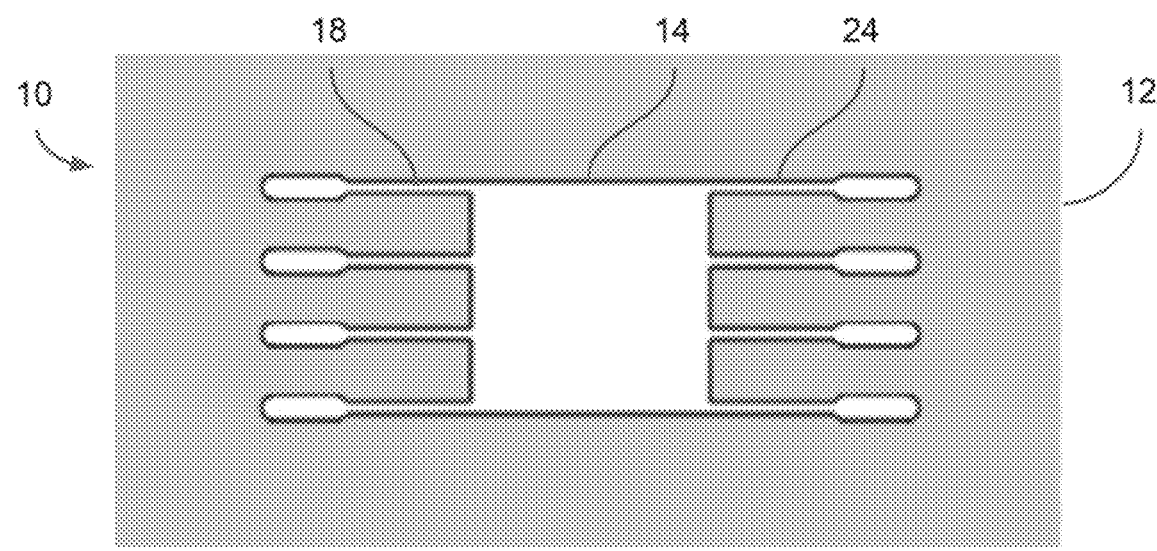
FIG. 20 shows an embodiment of the microfluidic device of the present invention having an equal number of upstream hydro-mincing microfluidic channels and downstream sieve microfluidic channels, causing the device to be symmetrical.

In some embodiments, the present invention features a system for the processing of a sample 16 into cellular suspensions. The system may include a tissue sample 16 having a size within the range of 1 mm 3 to 50 mm³. The system may further comprise a microfluidic device 10. The microfluidic device 10 is formed as a substrate or chip 12. The substrate or chip 12 may have an inlet 22, an outlet 28, and a sample chamber 14 dimensioned to hold the tissue sample 16 formed therein. The sample chamber 14 may be fluidically coupled at a first side to a plurality of upstream hydro-mincing microfluidic channels 18 disposed in the substrate or chip 12. The upstream hydro-mincing microfluidic channels 18 may be further fluidically coupled to the inlet 22. The sample chamber 14 may additionally be coupled at a second side to a plurality of downstream sieve microfluidic channels 24 disposed in the substrate or chip 12. The downstream sieve microfluidic channels 24 may be further fluidically coupled to the outlet 28. In some embodiments, the width of the upstream hydro-mincing microfluidic channels 18 and the width of the downstream sieve microfluidic channels 24 may be greater than 50 nm. In some embodiments, the width of the upstream hydro-mincing microfluidic channels 18 and the width of the downstream sieve microfluidic channels 24 may be smaller than the smallest dimension of the tissue sample 16. In some embodiments, the width of the sample chamber 14 may be within the range of about 0.5 mm and 1 cm. In some embodiments, the length of the sample chamber 14 may be less than 50 cm, and the height of the sample chamber 14 may be less than 5 cm. In some embodiments, the number of upstream hydro-mincing microfluidic channels 18 may be equal to the number of downstream sieve microfluidic channels 24 (see FIG. 20). The number of upstream hydro-mincing microfluidic channels 18 and downstream sieve microfluidic channels 24 and the width of the sample chamber 14 may depend on the size of the tissue sample 16 being processed. Tissue samples 16 with a smaller width may be processed more effectively than tissue samples 16 with a larger width.

Figure 21A:
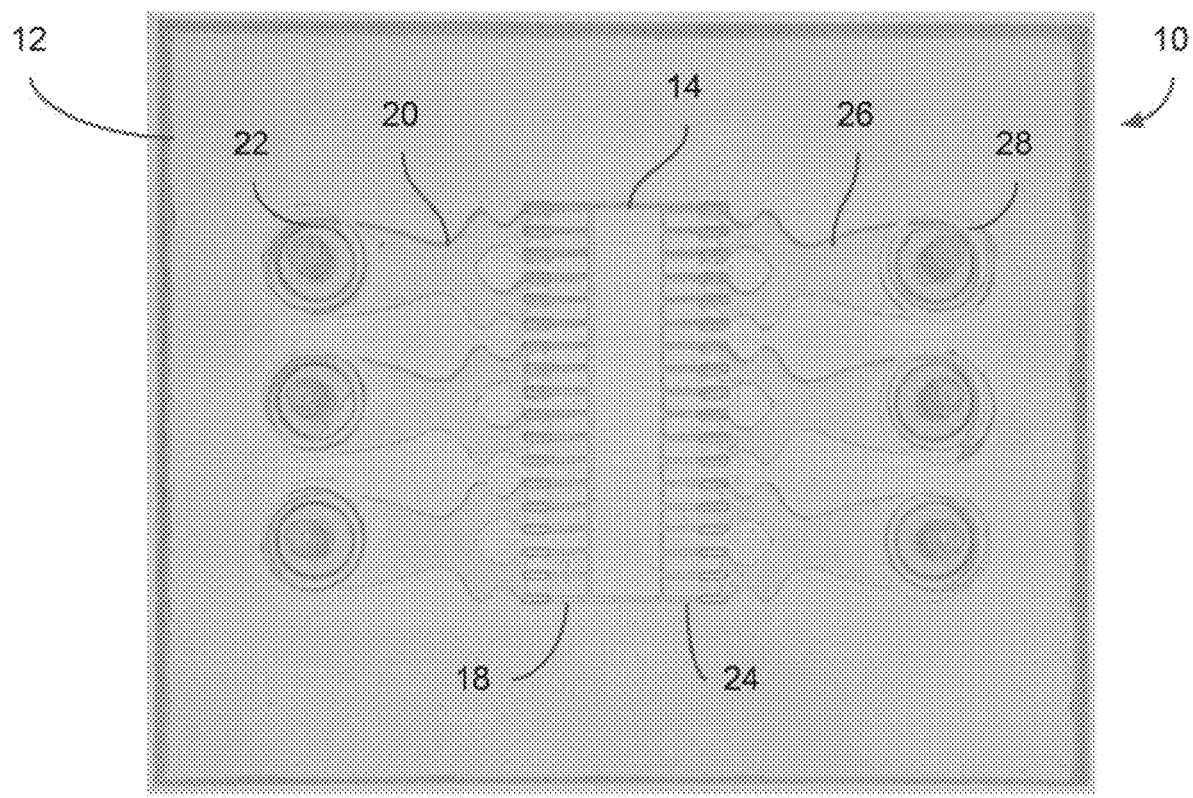
FIG. 21A shows a photograph of a plurality of microfluidic devices coupled in parallel at the sample chamber in order to process larger sample sizes.
Figure 21B:
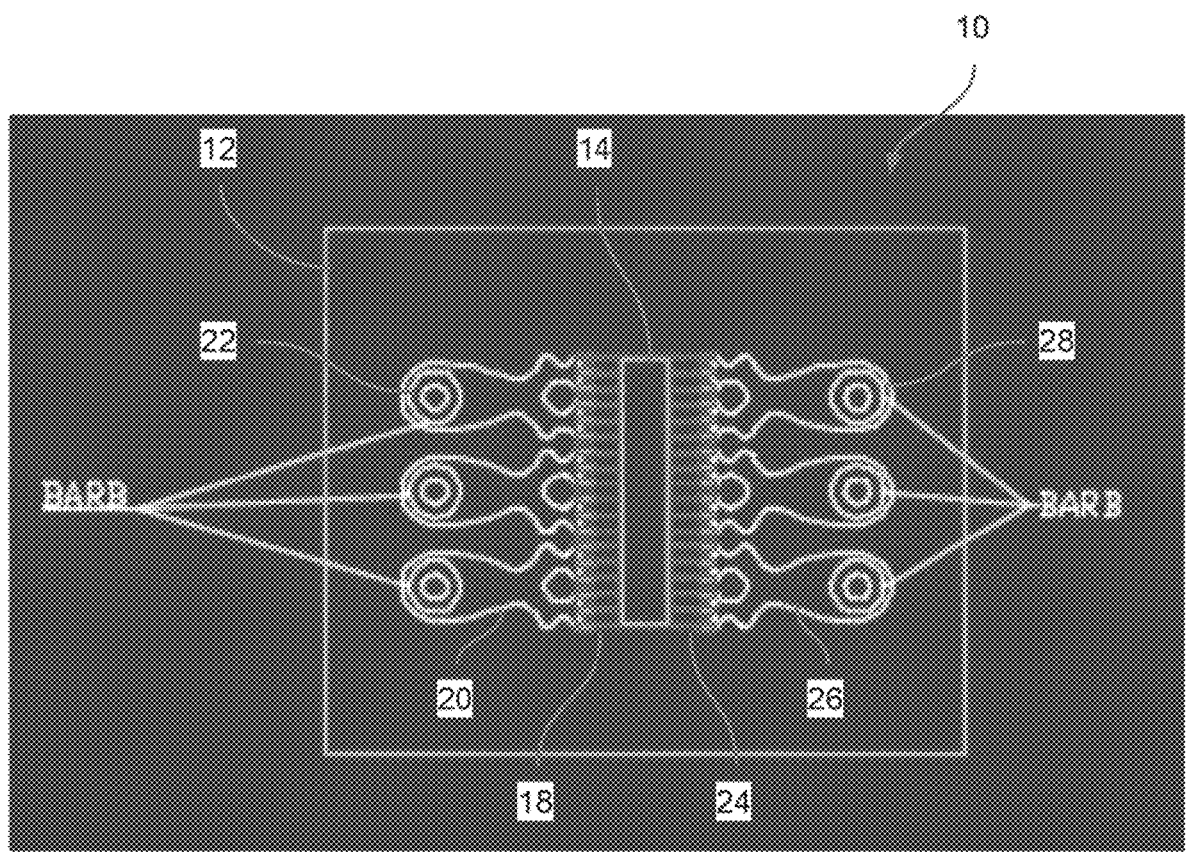
FIG. 21B shows a schematic of a plurality of microfluidic devices coupled in parallel at the sample chamber in order to process larger sample sizes.

In some embodiments, a first instance of the microfluidic device 10 may be coupled to at most two additional instances of the microfluidic device 10. The coupling may occur at a third side of the sample chamber 14 (e.g., a side), a fourth side of the sample chamber 14 (e.g., another side), or a combination thereof depending on how many instances of the microfluidic device 10 are coupled to the first instance of the microfluidic device 10. These different instances may be contained in the same substrate or chip 12 as seen in FIGS. 21A and 12B. FIGS. 21A-21B show embodiments of the aforementioned parallel coupling of microfluidic devices 10. This allows for an indefinite number of microfluidic devices 10 to be coupled to each other in parallel in order to process larger sample sizes without the need to lengthen or enlarge the device. The flow rate of fluid directed through the coupled microfluidic devices 10 may be proportionally increased depending on the number of instances of microfluidic devices 10 coupled together. In some embodiments, a different type of tissue sample 16 is placed in the sample chamber 14 of each instance of the microfluidic device. The type of tissue sample 16 processed by the present invention may be selected from a group comprising kidney tissue, liver tissue, heart tissue, lung tissue, breast tumor tissue, spleen tissue, and pancreas tissue.

The microfluidic device 10, in one embodiment, was designed to process samples obtained from core needle biopsies, directly into cell suspensions without the need for manual processing steps such as scalpel mincing. However, in other embodiments, the microfluidic device 10 processes a larger tissue sample after the sample has been subject to some mechanical processing (e.g., scalpel mincing). The particular size of the sample chamber 14 may vary depending on the size of the sample 16. Typically, the width of the sample chamber 14 may be within the range of about 0.5 mm and about 10 mm, the length of the sample chamber 14 is less than 2 cm, and the height of the sample chamber 14 is less than 1 cm. For example, with reference to FIG. 1, in one embodiment, the sample chamber 14 has a width 2 mm or less, the length of the sample chamber 14 is less than 2 cm, and the height of the sample chamber 14 is less than 2 mm (height dimension is perpendicular to the plane of the page). Fluid flows in the direction of arrows A along the width of the sample chamber 14. In another embodiment, the width of the sample chamber 14 is around 1.5 mm or less, the length of the sample chamber 14 is around 1 cm or less (e.g., approximately the size of a Tru-Cut® core biopsy needle; about 1 cm long×1 mm diameter tissue), and the height of the chamber is less than 2 mm (e.g., around 1 mm). In still other embodiments, the sample chamber 14 may be much smaller, for example, and can accommodate samples 16 having a longest dimension of around 1 mm. For example, when the sample 16 has been subject to some mechanical processing (e.g., mincing) the sample chamber 14 may have a much smaller size. The height of the sample chamber 14 may vary but is typically less than 1 cm and more typically less than 2 mm (e.g., a height of 1 mm may be used as described herein). In some embodiments, the sample chamber 14 is dimensioned to receive a sample 16 directly obtained from a tissue biopsy device such as the Tru-Cut® core biopsy needle or similar devices.

The second feature of the microfluidic device 10 includes a plurality of hydro-mincing microfluidic channels 18 located upstream of the sample chamber 14 which focus fluid into high velocity jets that are directed into the sample 16 retained in the sample chamber 14. The hydro-mincing microfluidic channels 18 as seen in FIG. 1 are fluidically coupled with an inlet channel 20 that receives fluid from an inlet 22. Fluid thus moves through the microfluidic device 10 in the direction of arrows A. The hydro-mincing microfluidic channels 18 produce fluid jets that concentrate hydrodynamic shear forces at discrete locations on the sample 16, breaking the sample 16 down mechanically and delivering proteolytic enzymes deep inside the sample 16 (i.e., tissue). This is analogous to manually mincing the tissue with a scalpel, and hence these are referred to as hydro-mincing microfluidic channels 18. The width of the hydro-mincing microfluidic channels 18 may vary but is generally within the range of about 50 µm to about 1 mm. For example, a width of the hydro-mincing microfluidic channels 18 within the range of about 100 µm to about 200 µm may be typical, although other dimensions outside this specific range may be used.

Finally, a plurality of downstream sieve microfluidic channels 24 are located downstream of the sample chamber 14 to act as a sieve that selectively retains larger pieces of tissue and cellular aggregates for further digestion. The downstream sieve microfluidic channels 24 form sieve gates that retain the larger sized tissue portions and cellular aggregates to prevent them from passing further downstream. Smaller aggregates and single cells are, however, allowed to pass out of the device 10 for collection or potentially for further microfluidic processing. For example, the cells that leave the device 10 may be subject to downstream cell sorting and/or analysis to create point-of-care platforms for cell-based diagnostics and therapies.

In one embodiment, the downstream sieve microfluidic channels 24 (along with the hydro-mincing microfluidic channels 18) are spaced evenly along the side or end of the sample chamber 14 to firmly secure the sample 16 in place in the sample chamber 14 and minimize backpressure. The width of the downstream sieve microfluidic channels 24 may vary but may be within the range of about 10 µm and 1 mm. More typically, the downstream sieve microfluidic channels 24 have a width within the range of about 100 µm to about 1 mm. For example, in some embodiments a width within the range of 500 µm to 1 mm is useful. During experiments described herein, a channel width of 500 µm for the downstream sieve microfluidic channels 24 was used and the device could comfortably accommodate seven (7) such channels across the width of the sample chamber 16. The plurality of downstream sieve microfluidic channels 24 lead to a common outlet channel 26 that extends to an outlet 28 where fluid can leave the microfluidic device 10.

In some embodiments, the width of the downstream sieve microfluidic channels 24 may be larger than the width of the hydro-mincing microfluidic channels 18. In other embodiments, the width of the downstream sieve microfluidic channels 24 may be smaller than the width of the hydro-mincing microfluidic channels 18. In still other embodiments, the width of the downstream sieve microfluidic channels 24 may be substantially the same as the width of the hydro-mincing microfluidic channels 18.

Figure 2:
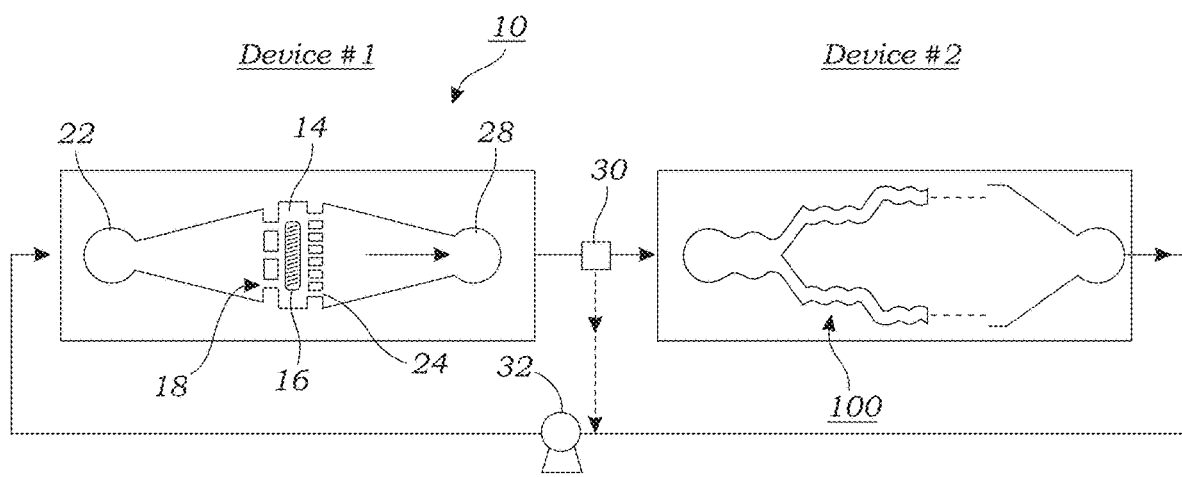
FIG. 2 illustrates a schematic illustration of a system that incorporates a microfluidic device for the processing and digestion of tissue with a secondary microfluidic device that is located downstream of the first device.

Note that 500 µm is comparable to the ~1 mm size of tissue pieces typically achieved by scalpel mincing. Aggregates of this size would also be ideal for directly inputting into a downstream branching channel array dissociation device such as that disclosed in U.S. Pat. No. 9,580,678, which is incorporated therein. FIG. 2 illustrates one such embodiment where the output from a first device (i.e., Device #1; microfluidic device 10) is then input into a second downstream device 100 (Device #2) for additional tissue dissociation.

For example, in one embodiment, the microfluidic device 10 is coupled to another tissue dissociation device 100 like that illustrated in the '678 patent. In that device 100, a series of stages of microfluidic channels with decreasing dimensions and having a series of expansion and constriction regions (illustrated in FIG. 2) are used to impart shearing forces on cell clusters and aggregates to dissociate tissue. The microfluidic device 10 can be coupled to such as device 100 as is illustrated in FIG. 2. In this embodiment, the output of the first microfluidic device 10 may be coupled to the input of the second microfluidic device 100 that is used for further tissue dissociation. A valve 30 may be located between the two devices (10, 100) to allow selective flow through the second tissue dissociation device 100. In addition, a pump 32 is illustrated that is used to recirculate flow between one or both of the microfluidic devices 10, 100. It should be understood, however, that rather than recirculating flow as illustrated, flow may pass directly through the devices without any recirculation.

Figure 22:
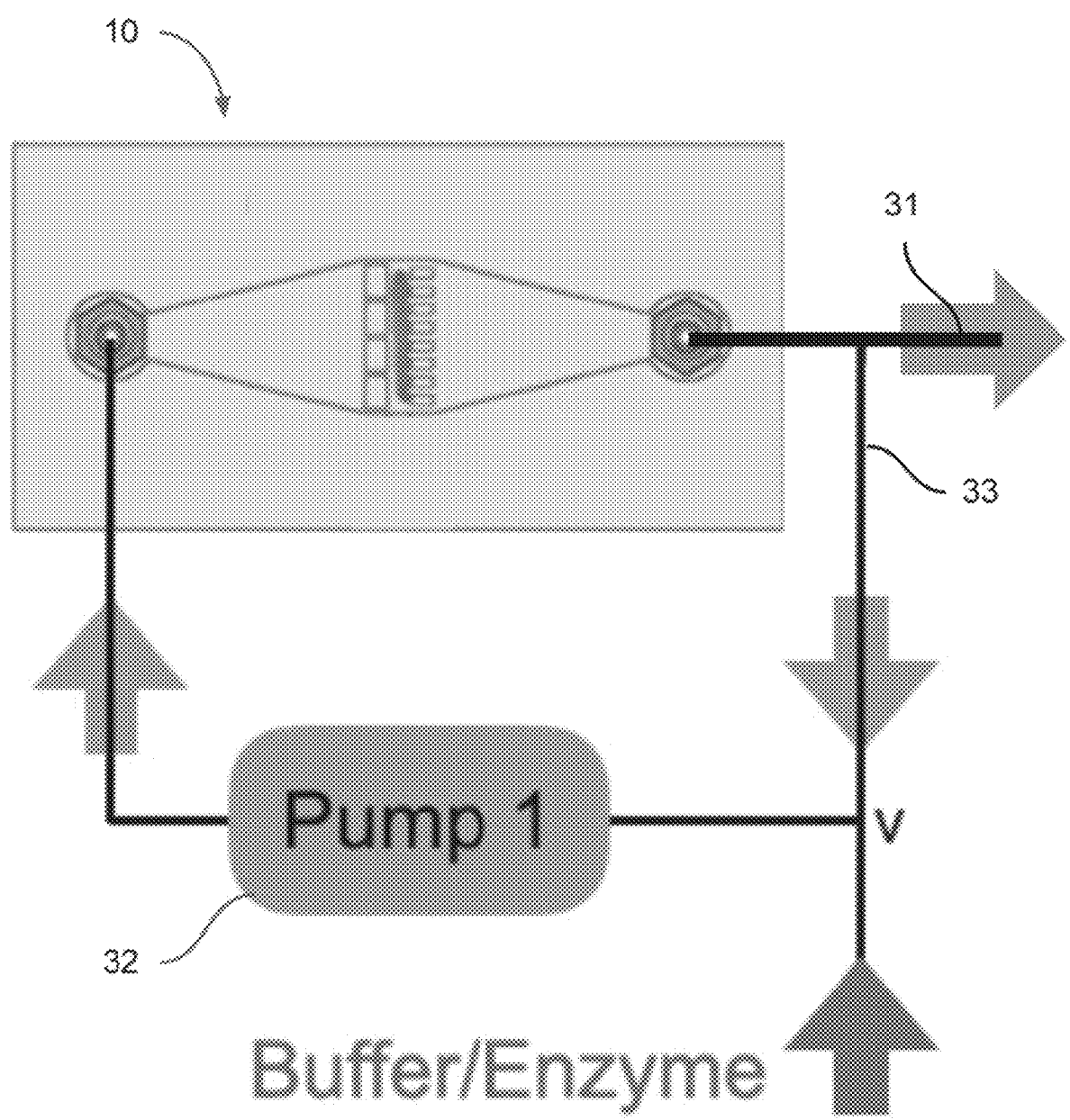
FIG. 22 shows a schematic of an embodiment of the present invention wherein the outlet is fluidly connected to a junction for directing pieces of digested tissue sample through an exit tube out of the system or recirculated back into the inlet of the device in order to further process the tissue sample. A digestive enzyme source is additionally fluidly connected to a digestive enzyme source for providing additional digestive enzyme to be introduced to the inlet of the microfluidic device to replace digested tissue samples that exit the system through the outlet.

In some embodiments, the outlet 28 of the microfluidic device 10 may be fluidly connected to a junction. The junction may be fluidly connected to both an exit tube 31 and a recirculation tube 33. The exit tube 31 may be configured such that the tissue sample 16 may be directed by the pump 32 through the exit tube 31 to a collection chamber. The recirculation tube 33 may be fluidly connected to the inlet 22 of the microfluidic device 10 and configured such that the digestive enzyme fluid directed through the microfluidic device 10 may be directed by the pump 32 through the recirculation tube 33 to the inlet 22. In some embodiments, the recirculation tube 33 may additionally be fluidly connected to a digestive enzyme source for providing additional digestive enzyme to be introduced into the microfluidic device 10 (see FIG. 22). This process is used to further process the tissue sample 16.

Figure 3:
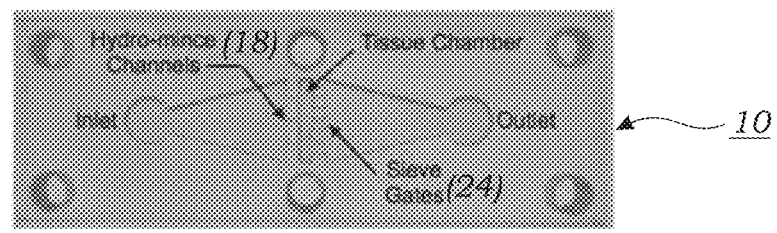
FIG. 3 illustrates a photographic image of a laser-etched acrylic sheet containing the chamber for loading tissue samples and fluidic "mincing" channels including upstream (left) for hydro-mincing and downstream (right) sieves (sieve gates).
Figure 4:
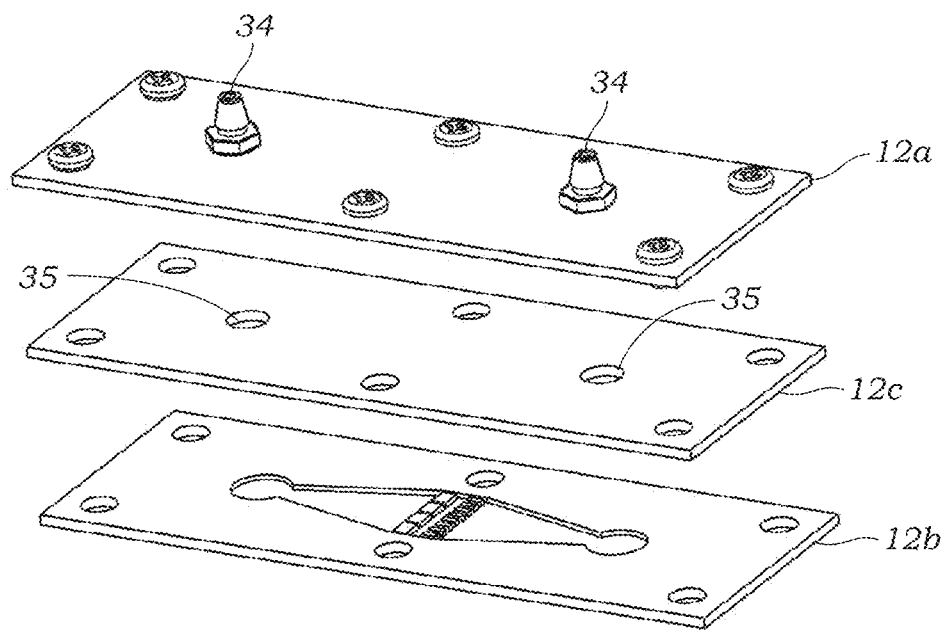
FIG. 4 illustrates an exploded view of a microfluidic device according to one embodiment that includes a polymer or elastic gasket layer sandwiched between two acrylic sheets or other hard plastic sheets. Hose barbs are illustrated in the top layer and nylon screws are used to hold the device together.
Figure 5:
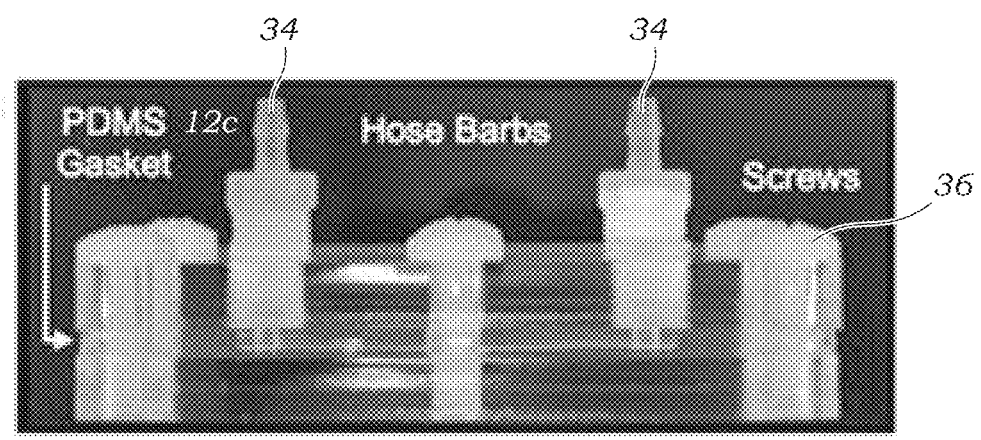
FIG. 5 illustrates a photograph of the fully assembled device illustrated in FIG. 4.

For the plurality of hydro-mincing microfluidic channels 18, the goal is to achieve efficient hydro-mincing. Using fewer channels would generate stronger fluidic jets, but would also cover less of the tissue cross-section and lead to higher device back-pressures. Since these are competing factors, experiments were conducted to use channel number as a test variable and created devices with three (3), five (5), and seven (7) hydro-mincing microfluidic channels 18. FIG. 3 illustrates a photograph of the microfluidic device 10 formed in hard acrylic sheets showing three (3) hydro-mincing microfluidic channels 18 and seven (7) downstream sieve microfluidic channels 24. Alternatively, materials for the microfluidic device 10 include polyethylene terephthalate (PET). FIG. 4 illustrates the multi-layered construction of the microfluidic device 10 according to one embodiment. In this embodiment, the microfluidic device 10 an upper substrate layer 12a formed from PET that includes the barbed ends or tubing connections 34 (e.g., hose barbs) that are fluidically coupled to the inlet 22 and outlet 28. The microfluidic device 10 further includes a lower substrate 12b that has the microfluidic features formed therein. This includes the inlet 22, inlet channel 20, sample chamber 14, downstream sieve microfluidic channels 24, outlet channel 26, and outlet 28 of FIG. 1. In this particular embodiment a polydimethylsiloxane (PDMS) gasket 12c having holes or vias 35 (for fluid access) is sandwiched between the upper substrate 12a and the lower substrate 12b which collectively together form the substrate/chip 12. Other elastic or polymers may be used for the gasket 12c. In this particular embodiment, fasteners 36 (e.g., screws) were used to secure the multiple substrates 12a, 12b, 12c together in a single construction as seen in FIG. 5.

As for channel size, smaller widths would generate stronger, more concentrated fluidic jets. Therefore, for experiments conducted on the microfluidic device 10 a width of 200 µm was chosen for the hydro-mincing microfluidic channels 18, which was the smallest feature resolution that could reliably be achieved with the laser-based fabrication method. It should be understood, however, that other dimensions may be used for the upstream hydro-mincing microfluidic channels 18 as well as the downstream sieve microfluidic channels 24.

Figure 6:
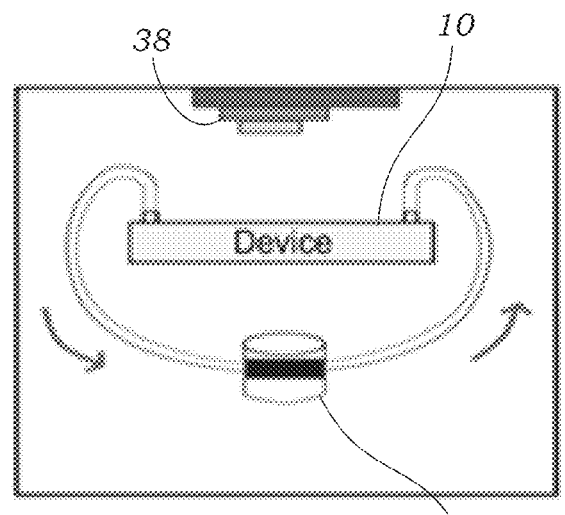
FIG. 6 schematically illustrates the experimental set-up used for digestion experiments using the microfluidic device for the processing and digestion of tissue. Flow was driven by a peristaltic pump and tissue digestion was visually monitored with a camera mounted above the device.

Devices 10 were fabricated in hard acrylic sheets using a laser to etch the sample chamber 14 and channel features of the hydro-mincing microfluidic channels 18, downstream sieve microfluidic channels 24, inlet channel 20, inlet 22, outlet channel 26, and outlet 28 in a first substrate 12*a* as described above. Laser power and raster speed were controlled to achieve a depth of approximately 1 mm, establishing channel height. A second layer of acrylic was used as the second substrate 12*b* and was tapped and fitted with hose barbs 34 to connect inlet and outlet tubing. Finally, the gasket layer 12*c* composed of polydimethylsiloxane (PDMS) was sandwiched between the acrylic layers 12*a*, 12*b* to provide a watertight seal. Note that the deformable nature of PDMS, and likely the tissue itself, should alleviate fluid flow and backpressure issues even while the tissue is initially obstructing the flow path. Finally, the assembled device sandwich 10 was held together using six (6) nylon screws 36 as seen in FIG. 5. The experimental set-up is shown in FIG. 6. For initial experiments, a peristaltic pump 32 was used to recirculate fluid through the device to conserve proteolytic enzyme solution. Of course, in an alternative embodiment, the flow may be continuous or the cells removed prior to recirculation in the device. In the experimental apparatus, a camera 38 was mounted above the microfluidic device 10 to monitor the progress of tissue digestion.

Figure 7:
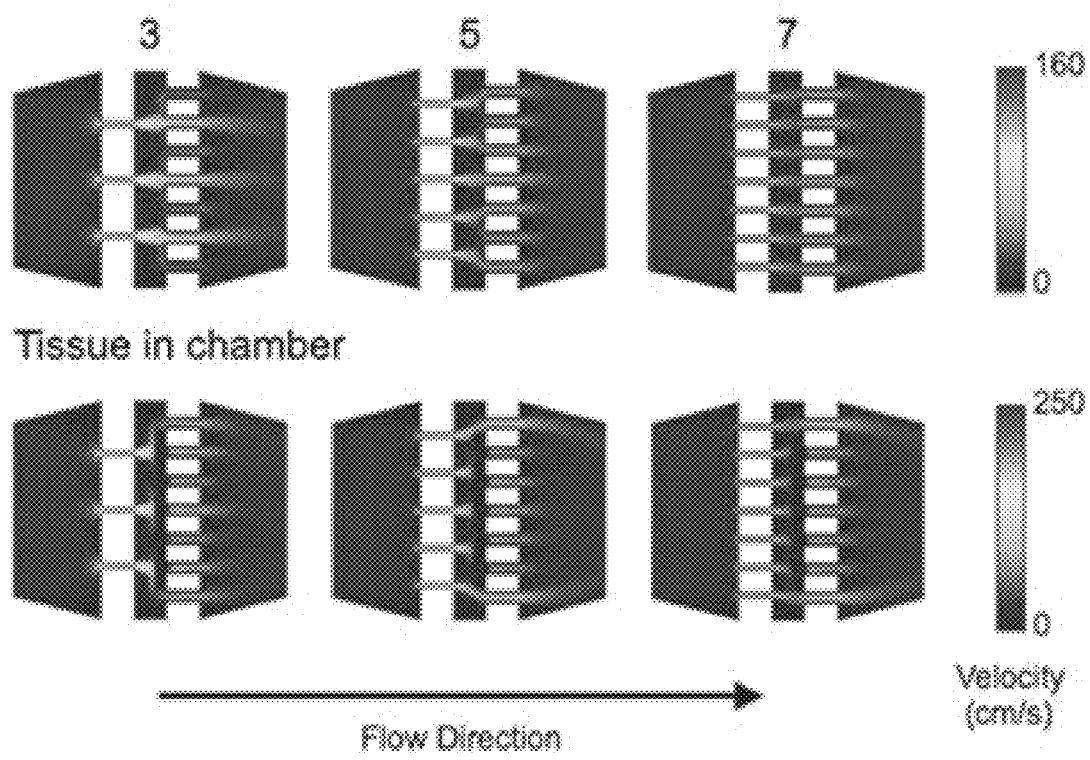
FIG. 7 illustrates finite-element fluid dynamics simulations showing velocity profiles in devices with different numbers of hydro-mincing microfluidic channels (3, 5, and 7). Simulation results are shown at 1 mL/min flow rate with the chamber empty and partially blocked by a model tissue. Fewer hydro-mince channels will generate stronger fluidic jets to shear the tissue, but with less overall coverage.

Computational fluid dynamics simulations were performed using COMSOL Multiphysics software for each three (3), five (5), and seven (7) hydro-mincing microfluidic channels 18 using a flow rate of 1 mL/min (FIG. 7). These simulations were performed with and without a model tissue within the sample chamber 14 to obstruct flow. As expected, the design with three (3) hydro-mincing microfluidic channels 18 generated the highest fluid velocities, or strongest fluidic "cuts." Increasing the number of hydro-mincing microfluidic channels 18 provided weaker "cuts" that were better dispersed across the tissue.

Figure 8A:
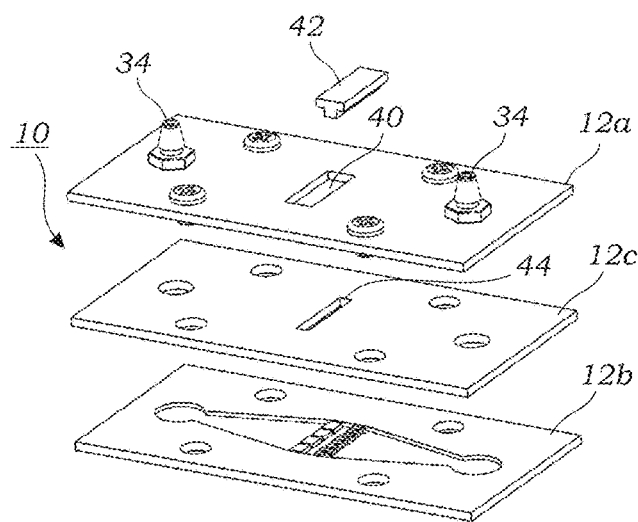
FIG. 8A illustrates an exploded view of another embodiment of a microfluidic device for the processing and digestion of tissue according to one embodiment.
Figure 8B:
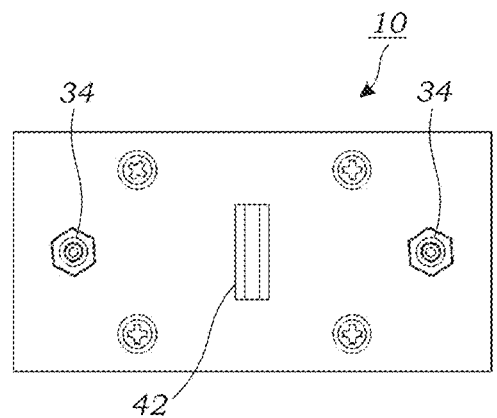
FIG. 8B illustrates a top or plan view of the microfluidic device of FIG. 8A.

FIGS. 8A, 8B, 9A, and 9B illustrate two alternative embodiments of a microfluidic device 10 that includes a feature to aid in loading the tissue or other sample into the sample chamber 16. The microfluidic device 10 includes a plurality of layers 12*a*, 12*b*, 12*c* that may be pressure laminated together with the aid of an adhesive or glue applied to the interface between adjacent layers to form the microfluidic device 10. Alternatively, the layers 12*a*, 12*b*, 12*c* may be secured together using fasteners such as those used in the embodiments of FIGS. 4 and 4. In the embodiment of FIGS. 8A and 8B, an open window 40 is provided on top layer 12*a* of the microfluidic device 10 through which sample 16 can be loaded using forceps. A plug 42 that is formed from silicon rubber material or the like is then placed in the window and secured with adhesive tape or glue. The middle layer 12*c* includes a hole or via 44 formed therein so that the sample 16 can be loaded into the sample chamber 14 formed in the first substrate 12*a*.

Figure 9A:
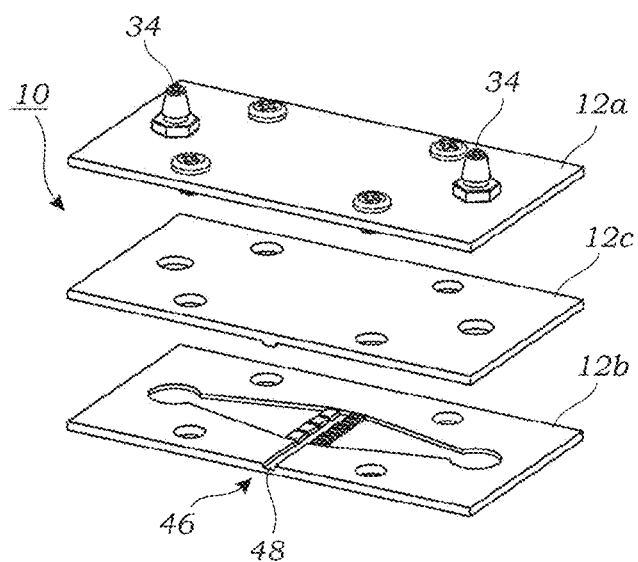
FIG. 9A illustrates an exploded view of another embodiment of a microfluidic device for the processing and digestion of tissue according to one embodiment.
Figure 9B:
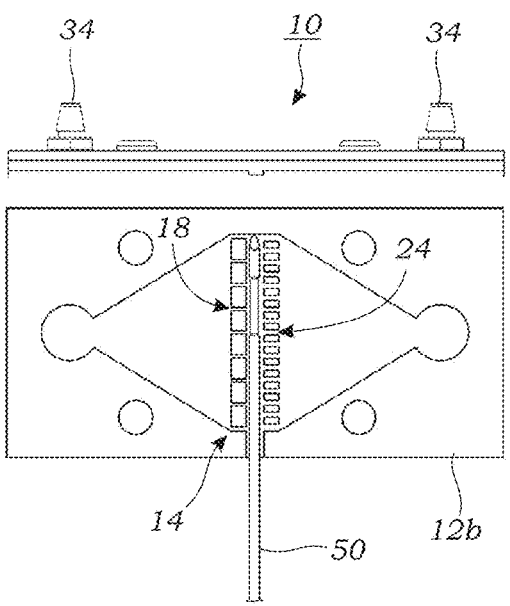
FIG. 9B illustrates a top or plan view of the microfluidic device of FIG. 9A.

In the embodiment of FIGS. 9A and 9B, the microfluidic device 10 has a sample port 46 located in the side of the microfluidic device 10 that can be used to load a sample 16 into the sample chamber 14. This design enables access through the side of the microfluidic device 10 by penetrating a silicon rubber septum 48 with a needle 50 as seen in FIG. 9B. In one embodiment, this needle 50 would be the same one used to extract the sample 16 (e.g., tissue), such as a core needle or punch biopsy. After penetrating the septum 48, the needle 50 would seat the sample 16 in the sample chamber 14 and remain in place (penetrating the septum 48) to seal the microfluidic device 10. In an alternative embodiment, the septum 48 may be a self-sealing septum 48 such that the needle 50 can be removed from the microfluidic device 10 without leakage of fluid or other contents outside of the microfluidic device 10.

Figure 10:
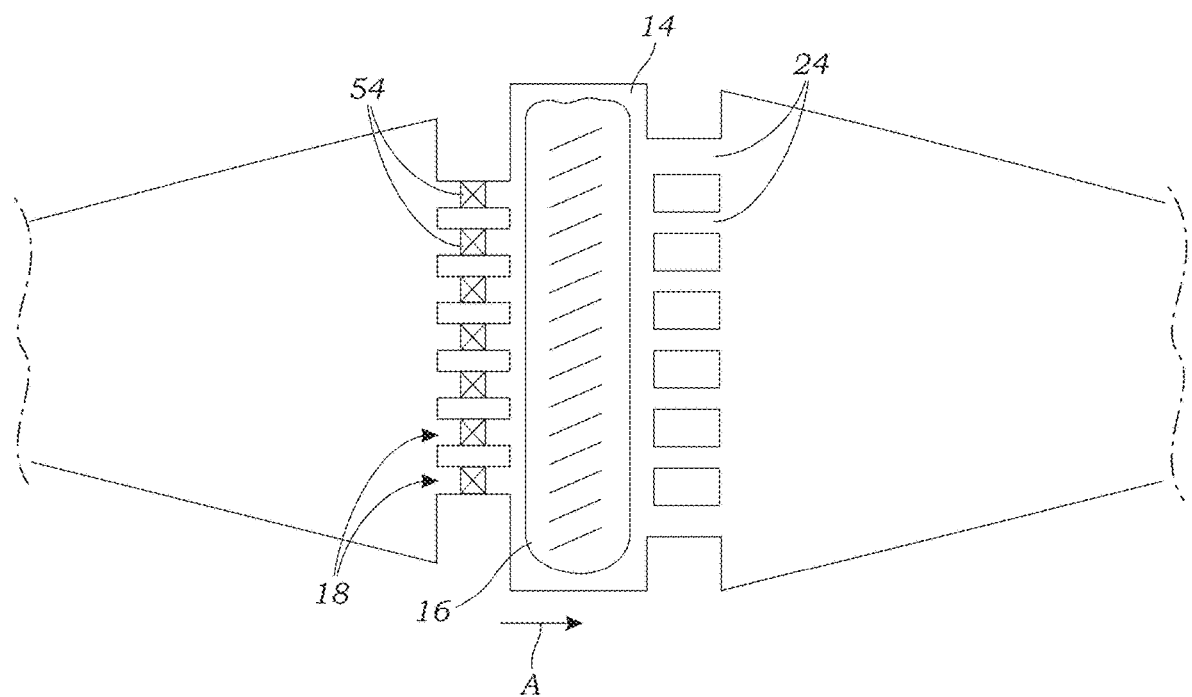
FIG. 10 illustrates another embodiment of a microfluidic device that includes valves located in the hydro-mincing microfluidic channels.

FIG. 10 illustrates one alternative embodiment of a microfluidic device 10 where one or more of the hydro-mincing microfluidic channels 18 can be selectively turned on or off by way of individual valves 54. The direction of fluid flow is indicated by arrow A in FIG. 10. In this regard, the option is provided to mince a large area of the sample 16 by sequentially using a small number of hydro-mincing microfluidic channels 18. For example, one or few of the hydro-mincing microfluidic channels 18 may be opened at any particular time so that high jetting or shearing forces are imparted on the sample 16. The valve(s) 54 may then be closed and another valve 54 or set of valves 54 that are aimed at a different region of sample 16 can then be turned on. The valves 54 may include microfluidic valves 54 that are known in the art. For example, microfluidic valves 54 that use a deformable membrane to actuate flow in a channel are known and may be used as one example. This process may continue for any number of cycles to mince the entire sample 16.

Figure 11:
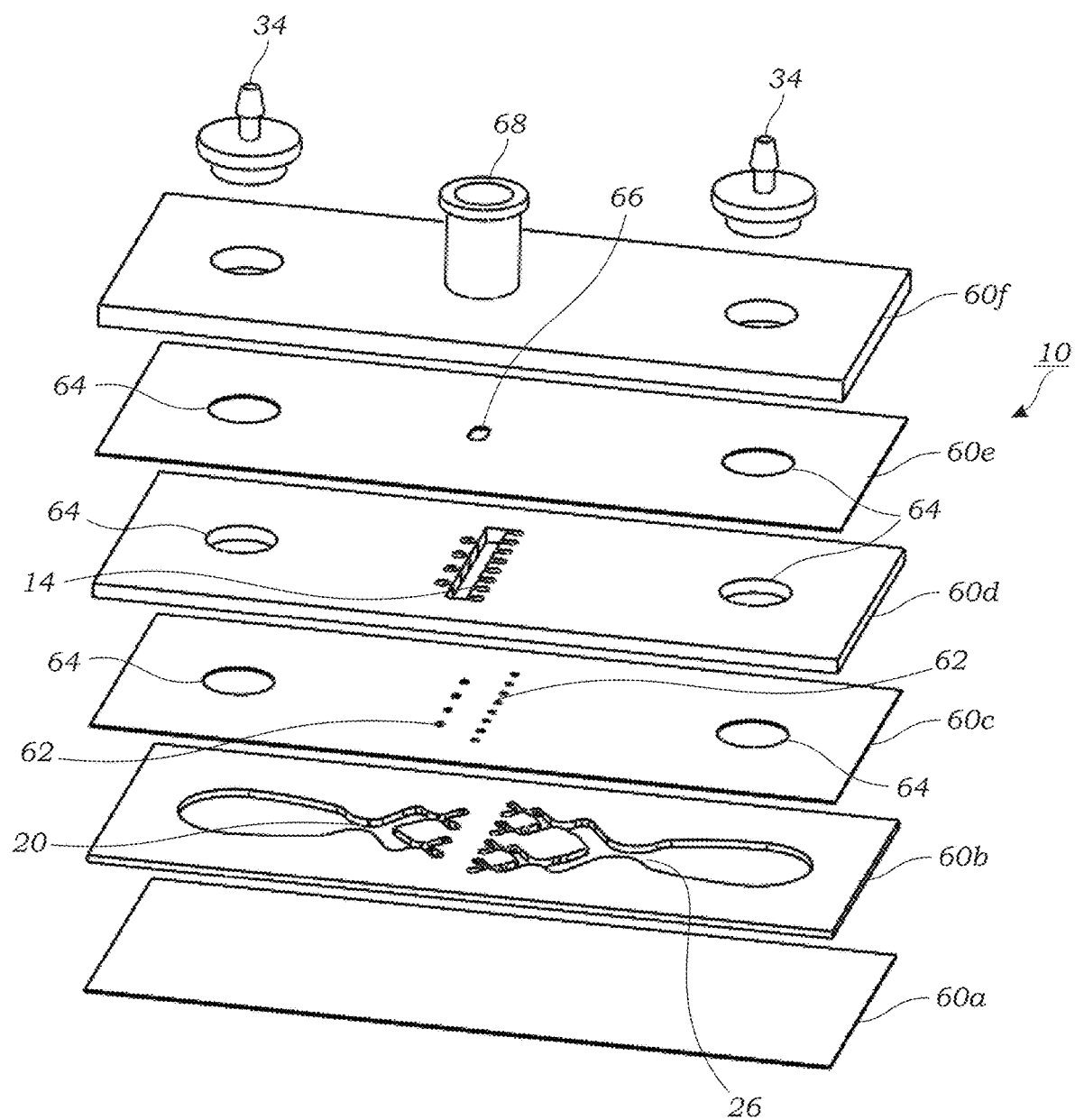
FIG. 11 illustrates an exploded view of another embodiment of a microfluidic device for the processing and digestion of tissue according to one embodiment.

FIG. 11 illustrates another embodiment of the microfluidic device 10. This microfluidic device 10 is formed from a multi-layer construction using hard acrylic or PET as described herein. In this embodiment, the microfluidic device 10 is formed from multiple layers 60*a*, 60*b*, 60*c*, 60*d*, 60*e*, and 60*f* The layers 60*a*, 60*b*, 60*c*, 60*d*, 60*e*, and 60*f* are pressure laminated together with the aid of an adhesive or glue (e.g., silicone or acrylic-based glues or adhesives) applied to the interface between adjacent layers to form the microfluidic device 10. Layer 60*a* serves as a base or bottom layer. Layer 60*b* has formed therein the inlet channels 20, outlet channels 26, as well as the hydro-mincing microfluidic channels 18 and downstream sieve microfluidic channels 24. Layer 60*c* has formed therein vias 62 that communicate with the inlet channels 20 and outlet channels 26 in layer 60*b* as well as apertures or holes 64 that provide access for the inlet 22 and the outlet 28. Layer 60*d* includes the sample chamber 14 formed therein that communicates with the vias 62 in layer 60*c*. Layer 60*d* further includes apertures or holes 64. Layer 60*e* includes in addition to the apertures or holes 64 a via 66 that provides access to the sample chamber 14. This via 66 may have a diameter of around 1 mm which is sized to accommodate sample 16 that has been mechanically processed (e.g., minced). Layer 60*f* is the top layer and includes barbed ends 34 that provide fluid access in/out of the microfluidic device 10. In addition, the layer 60*f* includes a loading port 68 that communicates with the via 66 and into the sample chamber 14. A cap (not shown) may be placed over the loading port 68 after loading so that fluid and tissue/cells remain inside the microfluidic device 10.

The loading port 68 may be configured as a Luer end that interfaces with a syringe or the like for loading. In this embodiment, minced sample 16 (e.g., minced tissue) is loaded into the loading port 68 prior to flowing fluid through the microfluidic device. In one alternative of this embodiment, the downstream sieve microfluidic channels 24 that communicate with the outlet channels 26 may include a filtering capability that restrict the passage of larger pieces of sample 16 from flowing downstream in the device 10. Filtering may also be provided by the vias 62.

Figure 12:
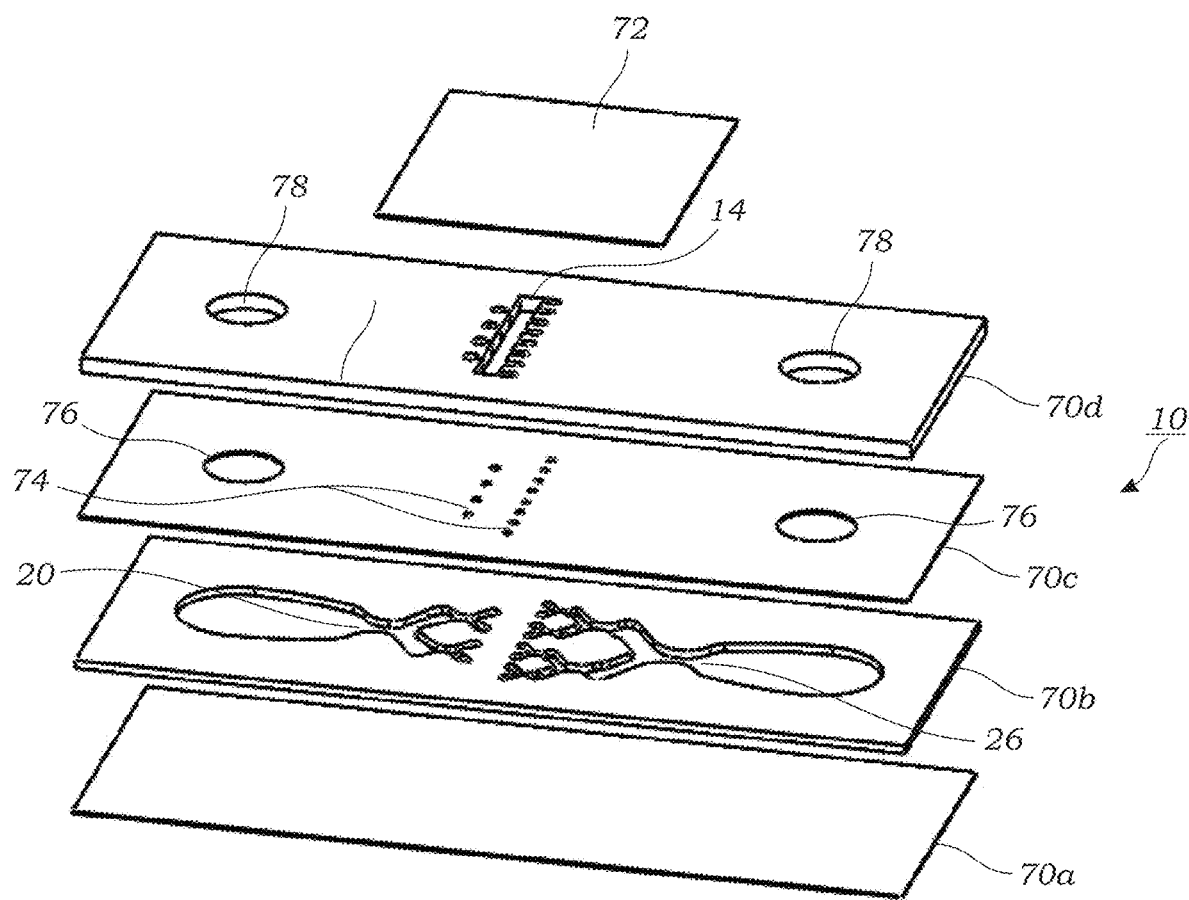
FIG. 12 illustrates an exploded view of another embodiment of a microfluidic device for the processing and digestion of tissue according to one embodiment.

FIG. 12 illustrates another embodiment of the microfluidic device 10. This microfluidic device 10 is formed from a multi-layer construction using hard acrylic or PET as described herein. In this embodiment, the microfluidic device 10 is formed from multiple layers 70*a*, 70*b*, 70*c*, 70*d* and includes a cap or lid 72 that, as explained herein, is used to close the device after the sample 16 has been loaded into the microfluidic device 10. The layers 70*a*, 70*b*, 70*c*, 70*d* are pressure laminated together with the aid of an adhesive or glue applied to the interface between adjacent layers to form the microfluidic device 10. Layer 70*a* serves as a base or bottom layer. Layer 70*b* has formed therein the inlet channels 20 and outlet channels 26. Layer 70*c* has formed therein vias 74 that communicate with the inlet channels 20 and outlet channels 26 in layer 70*b* as well as apertures or holes 76 that provide access for the inlet 22 and the outlet 28. Layer 70*d* includes the sample chamber 14 formed therein that communicates with the vias 74 in layer 70*c*. Layer 70*d* also includes apertures or holes 78 that can accommodate barbed ends 34 (not illustrated in FIG. 12) such as those illustrated in FIGS. 4, 5, 8A, 8B, 9A, 9B, and 11.

In this embodiment, the sample 16 can be loaded directly into the sample chamber 14. After loading the sample 16 in the sample chamber 14, the cap or lid 72 is then affixed to the layer 70*d* above the sample chamber 14 to seal the sample chamber 14 from the external environment of the microfluidic device 10. The cap or lid 72 may be secured to the layer 70*d* using an adhesive or the like. In some embodiments, the cap or like 72 may be removable so that the microfluidic device 10 can be used multiple times. In other embodiments, however, the cap or lid 72 is secured to the layer 70*d* in a permanent manner. As an alternative to an adhesive or glue, the cap or lid 72 may be secured to the layer 70*d* using one or more fasteners (not shown) such as clamps, screws, bands, clips, or the like.

Figure 13A:
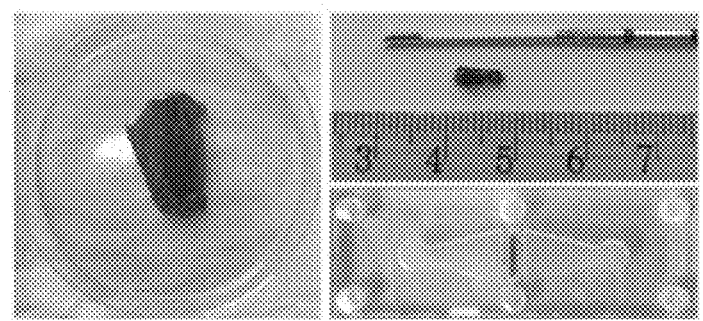
FIG. 13A is a photographic image of a tissue core obtained using a Tru-Cut™ biopsy needle and placed inside the tissue chamber.
Figure 13B:
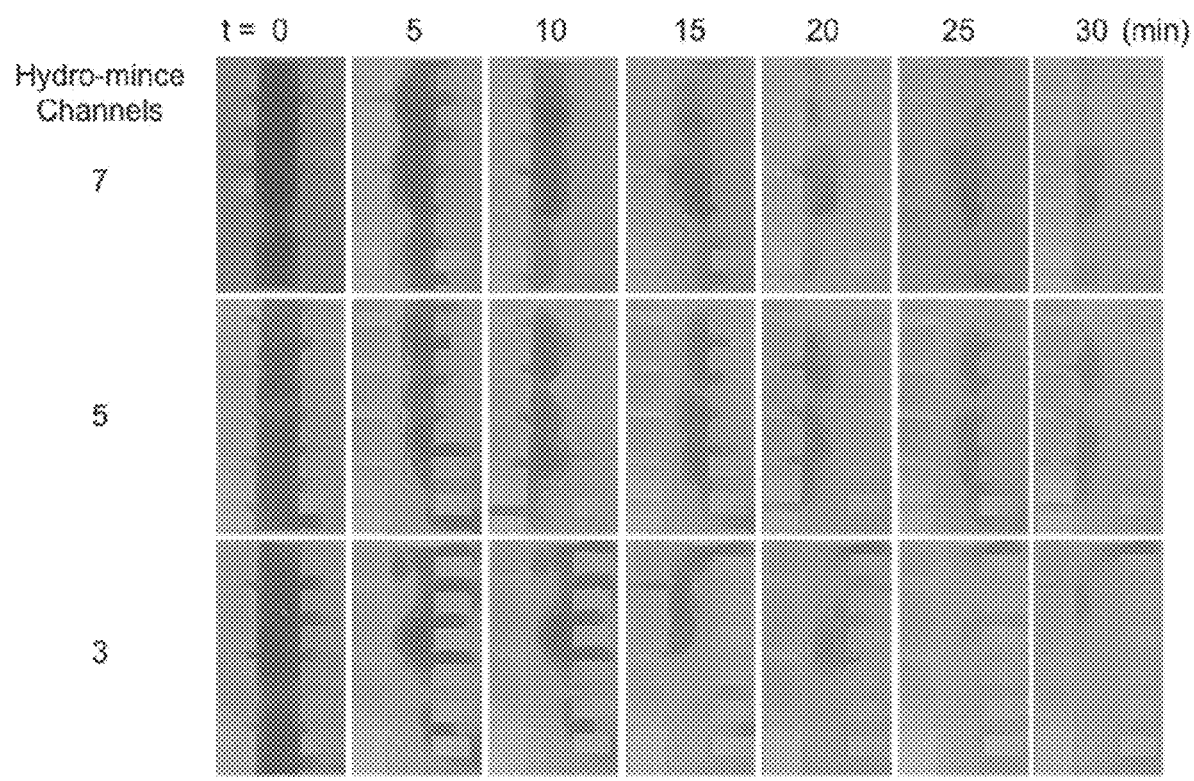
FIG. 13B illustrates time-lapse images of tissue digestion for devices with 3, 5, and 7 hydro-mincing microfluidic channels. The fluid contained collagenase, and was pumped through the device at 20 mL/min.
Figure 13C:
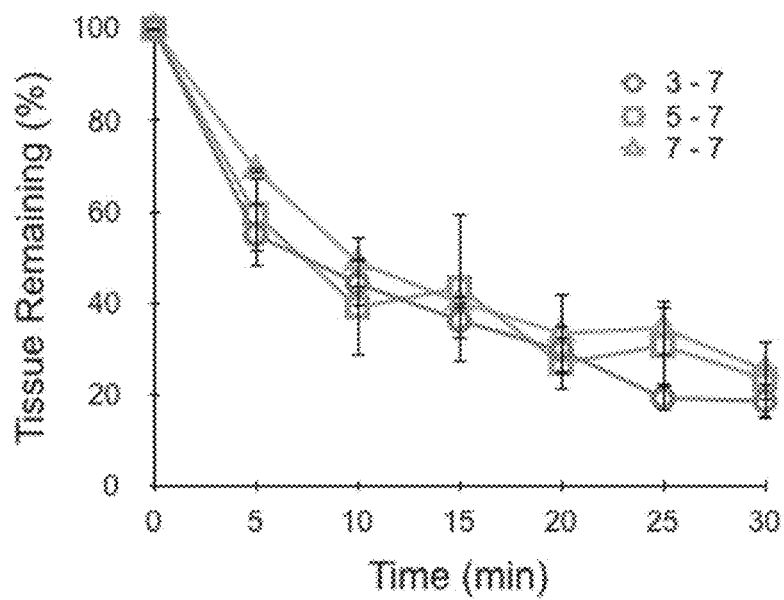
FIG. 13C illustrates a graph showing tissue loss as a function of time. Tissue loss was quantified from images based on mean gray value and overall tissue area. Trends were similar for each design, but variability was lowest for 3 hydro-mincing microfluidic channels.
Figure 13D:
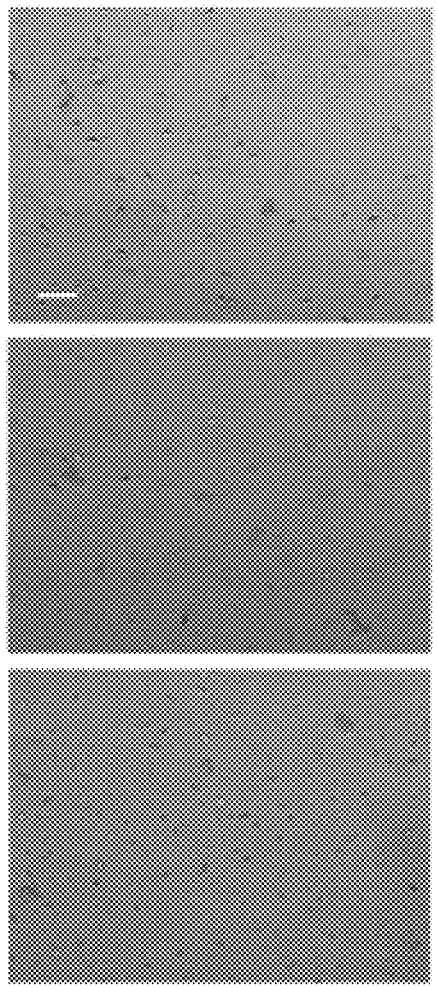
FIG. 13D illustrates micrograph images of device effluents after 30 min operation. Top is seven (7) hydro-mincing microfluidic channels. Middle is five (5) hydro-mincing microfluidic channels. Bottom is three (3) is hydro-mincing microfluidic channels. Scale bar is 100 µm. Error bars represent standard errors from at least three independent experiments.
Figure 14:
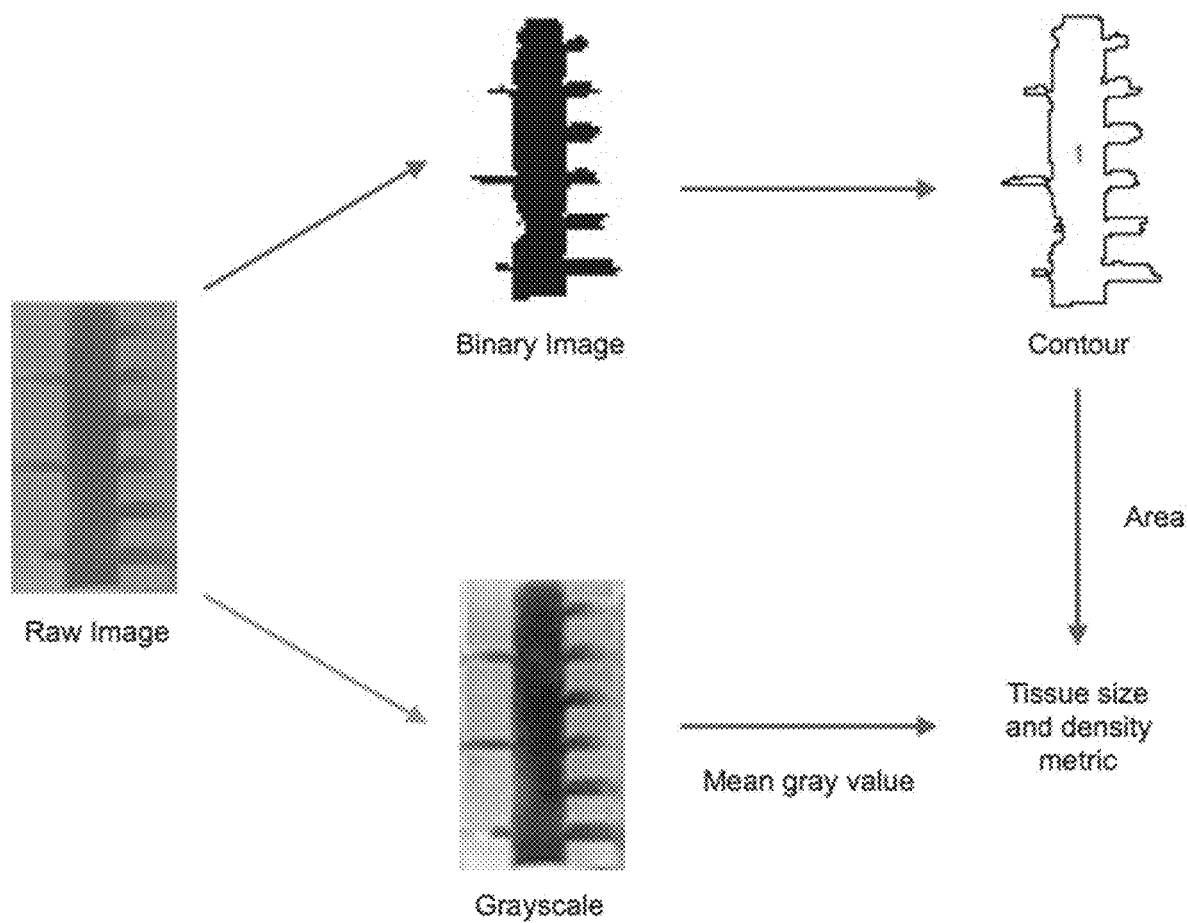
FIG. 14 illustrates an image processing algorithm used to monitor tissue digestion. Images were analyzed for tissue size and density to quantify changes during digestion within the device. First, raw images were separately converted to binary (upper arrow) and grayscale (lower arrow) images to outline the contour and quantify mean gray value, respectively. The area within the tissue contour was then calculated, and multiplied by mean gray value to obtain a single metric accounting for tissue size and density.

Initial Device Optimization Using Beef Liver Tissue. Performance of the microfluidic digestion device such as that illustrated in FIG. 1 was first evaluated using beef liver as the sample tissue. Model tissue cores were extracted using a Tru-Cut® biopsy needle and loaded into the sample chamber 14 (FIG. 13A). Devices were then primed with PBS buffers containing collagenase, sealed, and flow was initiated at 20 mL/min, the highest flow rate that could be achieved with the peristaltic pump. Images of tissue specimens were acquired every 5 min using the camera 38 mounted above the device as seen in FIG. 6 to monitor digestion, and experiments were performed for a total of 30 min (FIG. 13B). After each image was acquired, flow was briefly reversed to clear tissue that had seeped into the sieve microfluidic channels. Tissue seeping was most extensive using three (3) hydro-mince channels, reflecting the higher hydrodynamic forces being generated. Images were processed using ImageJ and MATLAB to assess the amount of liver tissue remaining in the device at each time point based on tissue area and pixel density (see FIG. 14). Digestion profiles are plotted in FIG. 13C, after normalizing by initial tissue mass. Results were nominally similar for all three devices, with a dramatic 40% tissue decrease during the first 5 min, followed by a more gradual decrease in tissue by ~10% per 5 min interval. The initial drop primarily correlated to diminished pixel density, which may have reflected tissue debulking or washing out of red blood cells. The subsequent gradual phase primarily reflected a loss of tissue mass. After 30 min, approximately 80% of the tissue had been removed from all three of the device designs. However, the device with three (3) hydro-mincing microfluidic channels provided the most consistent results in terms of lower variability between experiments, particularly at later time points, and thus was chosen for further evaluation. Representative micrographs of device effluents collected after 30 min device processing are shown in FIG. 13D. For all cases, sample effluents primarily comprised a mixture of larger tissue aggregates, tissue cells, and red blood cells.

Evaluation of Cell Suspensions Obtained from Fresh Mouse Organs.

Figure 15A:
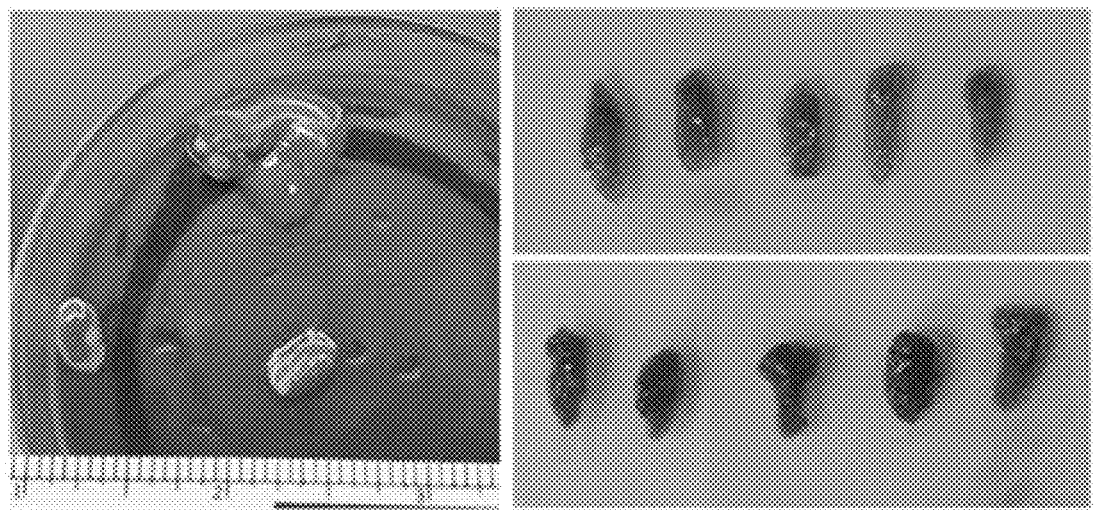
FIG. 15A illustrates photographic images of mouse liver (top right) and kidneys (bottom right) were freshly harvested and cut into 1 cm long×1 mm diameter pieces and placed within the device sample chamber.
Figure 15B:
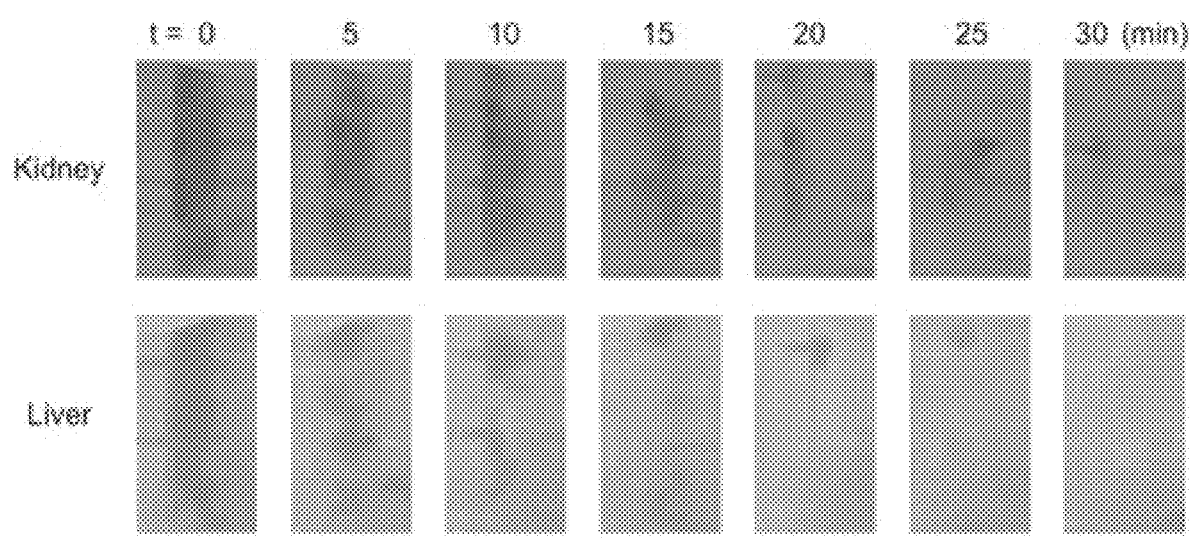
FIG. 15B illustrate time-lapsed images of tissue digestion for devices containing 3 hydro-mincing microfluidic channels. Tissue size and density both decreased over time as digestion progressed.
Figure 15C:
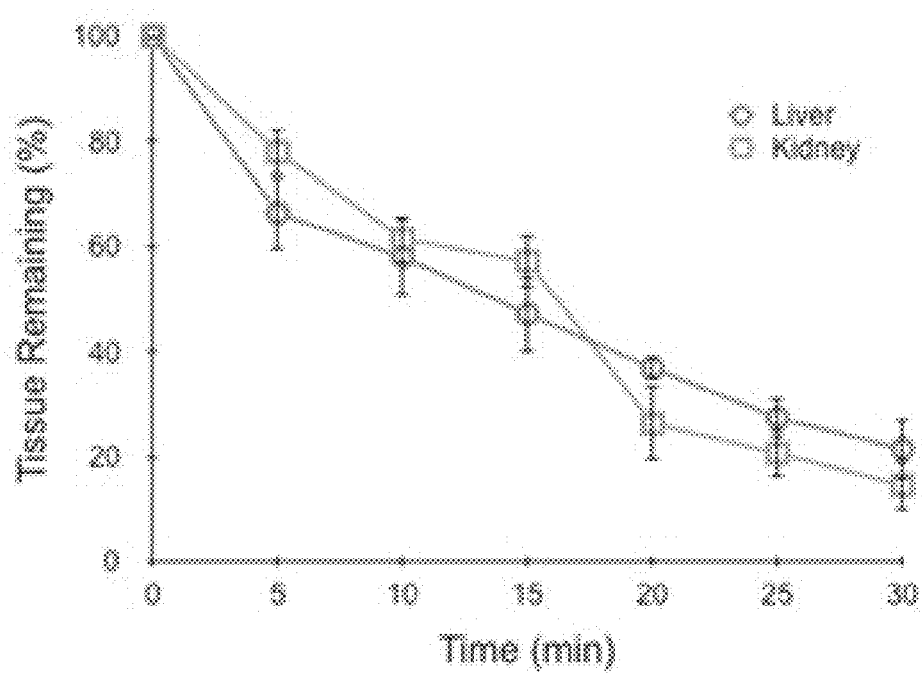
FIG. 15C illustrates a graph of tissue loss quantified from images based on mean gray value and overall tissue area, with liver and kidney samples demonstrating similar trends.
Figure 15D:
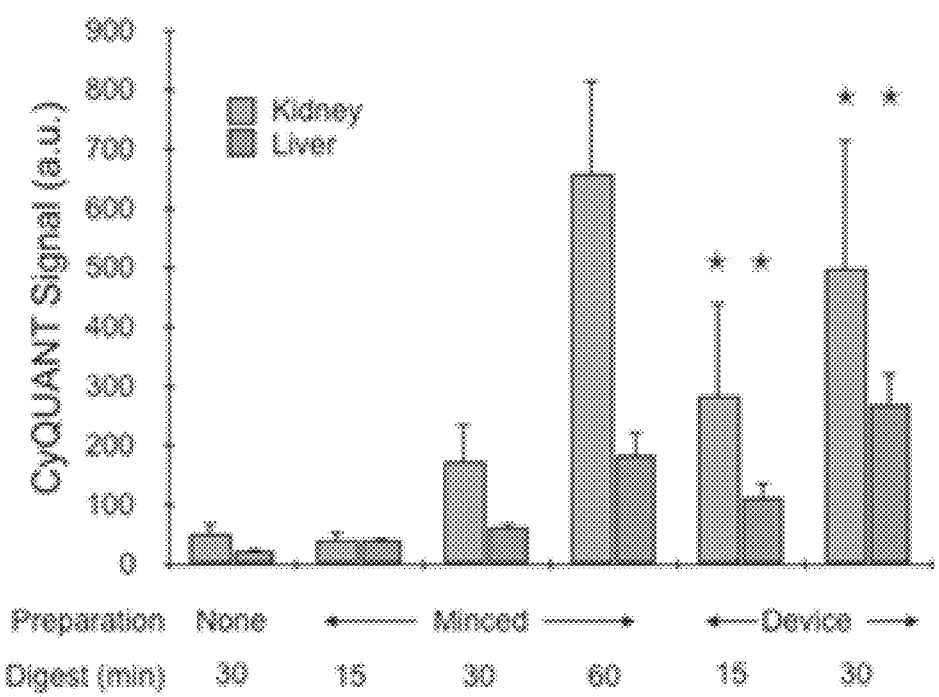
FIG. 15D illustrates a graph illustrating the results of the CyQUANT® assay was used to directly quantify cell suspensions obtained by digestion only, scalpel mincing and digestion, or device treatment lasting for a total of 15, 30, or 60 min. The CyQUANT® signal increased with treatment time, and was higher overall for kidney samples. Signals from device treated samples were consistently higher than minced controls, similar to gDNA and cell counting results presented in FIG. 3 of the main text. Error bars represent standard errors from at least three independent experiments. * indicates p<0.05 relative to minced control at the same digestion time.
Figure 16A:
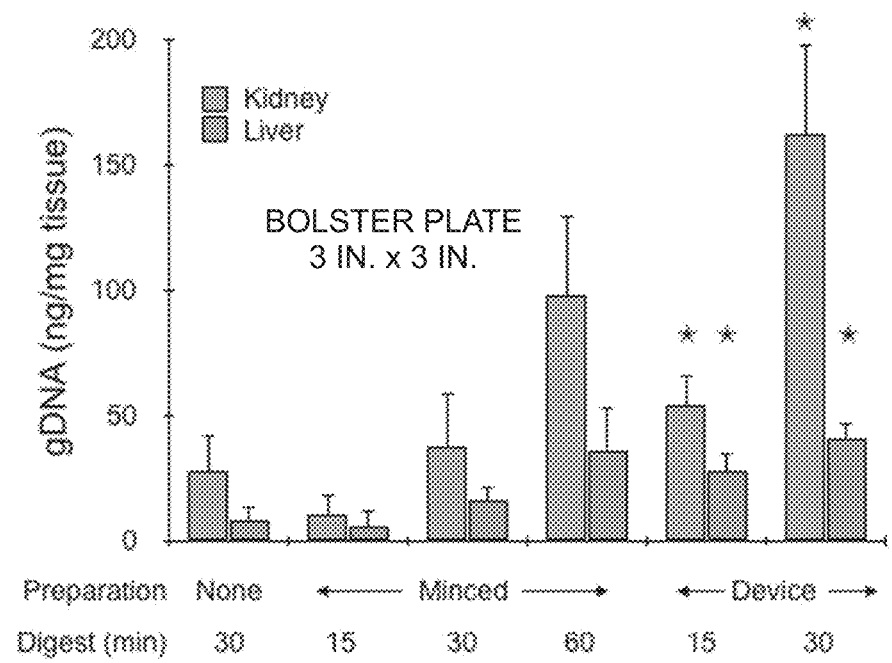
FIG. 16A illustrates a graph showing the amount of genomic DNA (gDNA) that was extracted and quantified from kidney and liver tissue cell suspensions obtained by digestion only, scalpel mincing and digestion, or device treatment lasting for a total of 15, 30, or 60 min. As seen in the graph, gDNA increased with treatment time, and overall was higher for kidney samples. Device treatment consistently provided more gDNA than minced controls at the same time point. In most cases, gDNA was also higher than the next digestion time point, although differences were not significant.
Figure 16B:
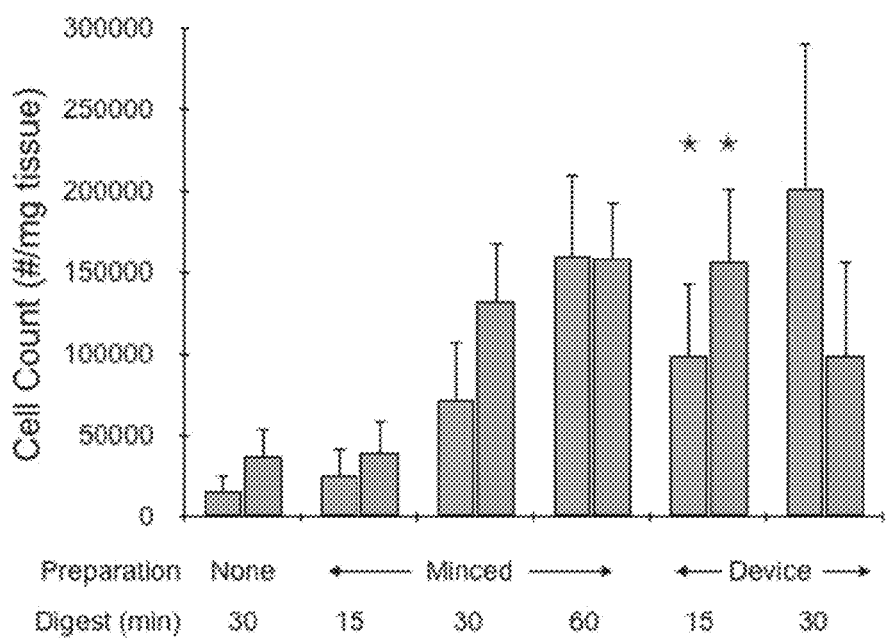
FIG. 16B illustrates a graph showing cell counter results, showing that single cell numbers largely matched gDNA findings but with higher variability. Also, liver values were now similarly comparable to kidney, suggesting that kidney suspensions may have contained more aggregates. Error bars represent standard errors from at least three independent experiments. * indicates p<0.05 relative to minced control at the same digestion time.
Figure 16C:
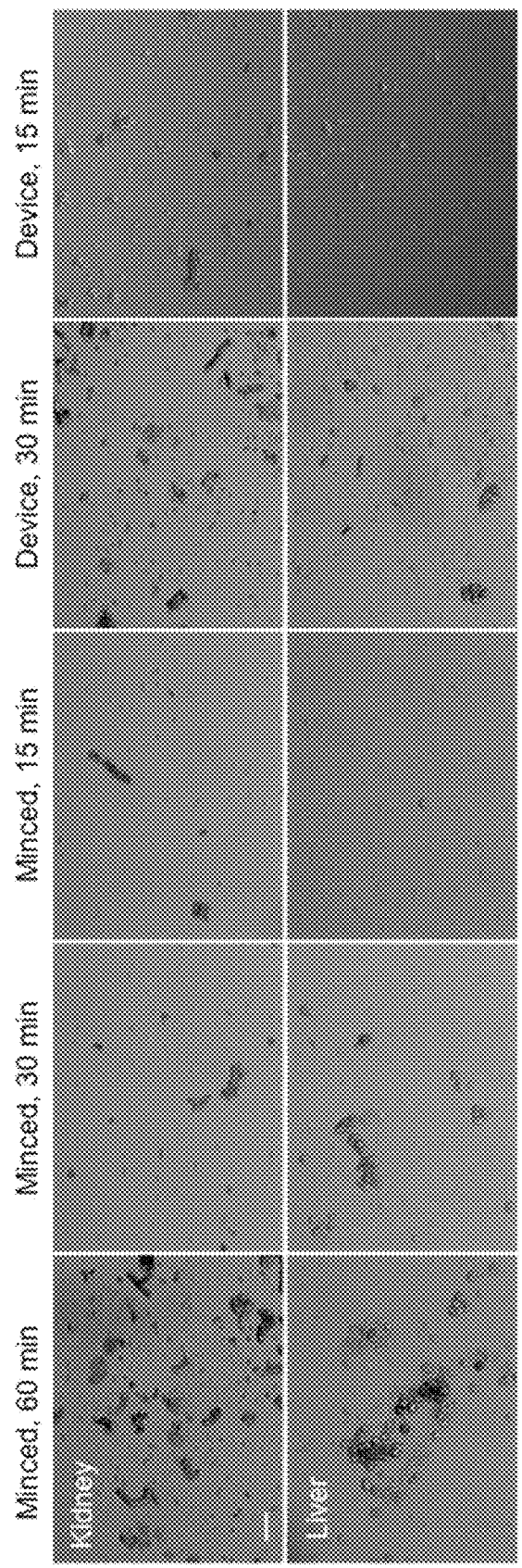
FIG. 16C illustrates micrographs of minced controls and device effluents after lysing red blood cells. Note the large number of aggregates in the controls, particularly at 60 min. Scale bar is 100 μm.

Next, the three (3) hydro-mincing channel design was tested using freshly resected murine liver and kidney samples. These live tissues better represent samples that will be used in future applications, and the resulting cell suspensions can be directly assayed for quality. Liver is generally considered to be among the easiest tissues to dissociate, but hepatocytes are well known to be fragile. Kidney is considered to be a difficult tissue to dissociate due to its structure as a dense array of blood vessels and epithelial lined tubules, which function under high physiologic hydrodynamic pressures, have tight intercellular junctions, and have specialized basement membranes. Immediately after harvesting, tissues were cut into ~1 cm×1 mm×1 mm pieces with a scalpel (see FIG. 15A) and weighed. Digestion device experiments were then conducted as described for beef liver, with collagenase recirculated for either 15 or 30 min before sample collection. Images were again taken every 5 min and processed to monitor tissue loss, which was similar to beef liver (see FIGS. 15B and 15C). Controls were further minced with a scalpel into ~1 mm$^3$ pieces before digesting with collagenase for 15, 30, or 60 min in a conical tube. These samples were constantly agitated, and vortexed every 5 min. A separate control was included in which the tissue was not minced, only digested for 30 min. Following digestion, device-processed and control samples were mechanically treated by vortexing and pipetting, filtered through a 70 μm cell strainer, and treated with DNase to remove extracellular DNA. Cellular content was then assessed based on total genomic DNA (gDNA) extracted using a QIAamp® DNA kit. For minced controls, gDNA progressively increased with digestion time (FIG. 16A). Kidney samples yielded approximately 100 ng gDNA per mg of tissue after 60 min digestion, while liver was less than half this value. Slightly less gDNA was obtained from the un-minced controls, but differences were not significant. Device treatment yielded dramatically more gDNA than controls when compared at the same digestion time. The difference was approximately 5-fold for both tissue types after 15 min, and 3 to 4-fold after 30 min. Moreover, device treatment produced at least as much gDNA as the minced control at the next longer digestion time point. Thus, the microfluidic digestion device can significantly improve digestion efficiency and shorten digestion time. DNA was also assessed within intact cellular suspensions using the CyQUANT® assay, which corroborated gDNA results (see FIG. 13D). Finally, a representative sample of each cellular suspension was treated with red blood cell lysis buffer before quantification of cell number with an automated counter and visualization of cells under phase contrast microscopy. Cell counts, which primarily reflected single cells but may also include some small clusters, were similar to gDNA results (FIG. 16B). The main difference was that liver now provided values that were comparable to kidney. This suggests that a significant portion of kidney cells may have remained in aggregates that could have passed through the cell strainer and been lysed to obtain gDNA. Alternatively, the cell counter may have detected more debris in liver suspensions, which was seen in micrographs for both minced controls and device treated samples (FIG. 16C).

Analysis of Cell Types, Numbers, and Viability Using Flow Cytometry.

The final evaluation focused on determining single cell numbers and viability. Fresh mouse kidney and liver samples were prepared and digested as described in the previous section, except the un-minced control was removed and a 10 min device treatment was added. Digested cellular suspensions were filtered through a 40 μm cell strainer and labeled with a panel of four fluorescent probes: CellMask™ Green to stain phospholipid cell membranes, Draq5 to stain DNA within all cells, 7AAD to stain DNA only within dead cells with disrupted plasma membranes, and CD45 to stain leukocytes (Table 1 below).

TABLE 1

| Assay | CellMask ™ Green (Lipid Membrane) | Draq5 (Nucleus) | CD45-PE (Leukocytes) | 7AAD (Dead Cells) |
|---|---|---|---|---|
| Red blood cells | + | − | − | − |
| Leukocytes | + | + | + | +/− |
| Tissue cells | + | + | − | +/− |

Figure 17:
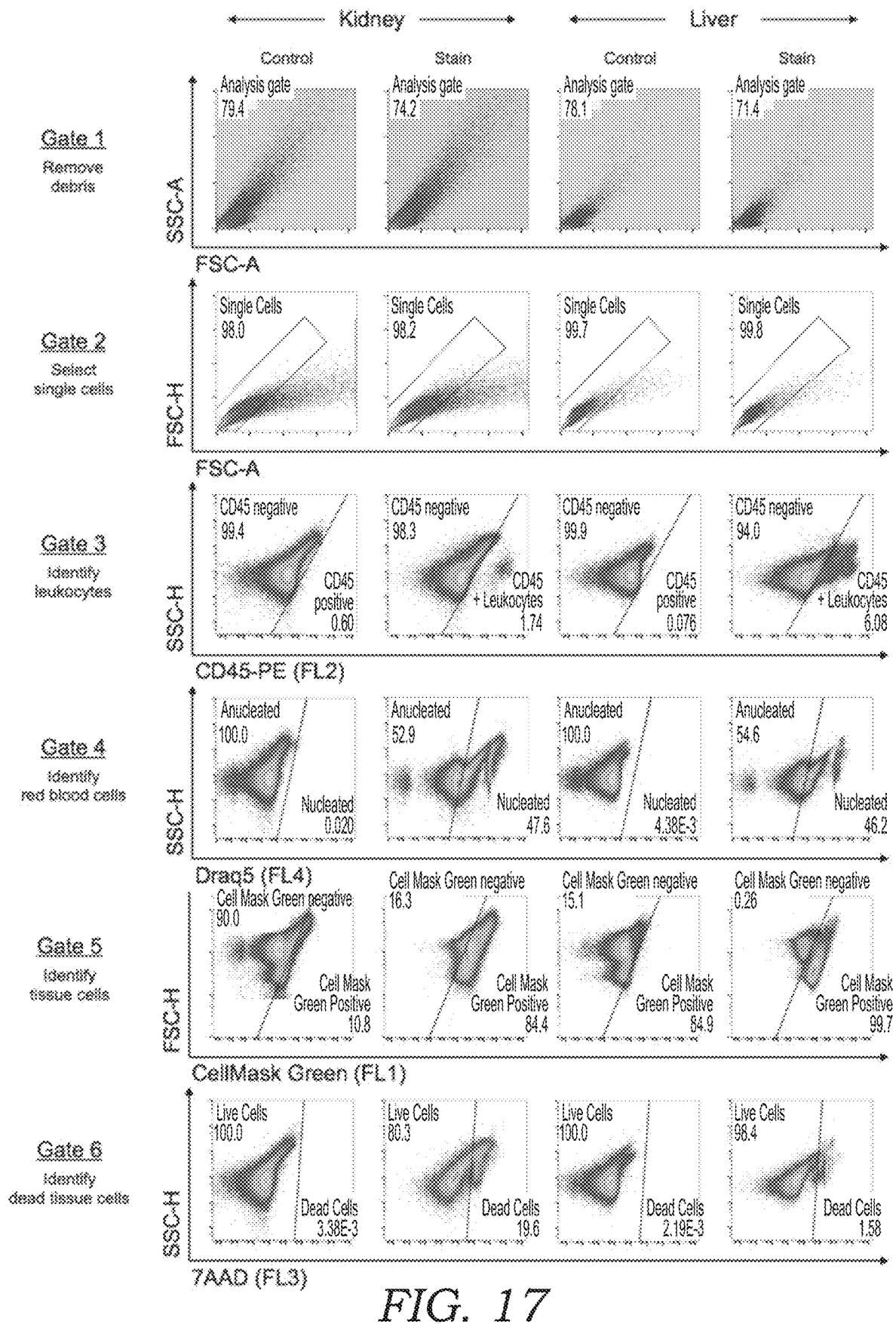
FIG. 17 illustrates FACS gating data for cell suspensions obtained from digested mouse and liver and kidney samples. Cell suspensions obtained from digested mouse liver and kidney samples were stained with the four-probe panel listed in Table 1 and analyzed using flow cytometry. Controls were treated only with an isotype matched (IgG2b), PE-conjugated antibody. Acquired data was assessed using a sequential gating scheme. First, an FSC-A vs. SSC-A gate (Gate 1) was used to exclude debris near the origin. Gate 2 was based on FSC-A vs. FSC-H, and was used to select single cells. Gate 3 distinguished CD45+ leukocytes based on CD45-PE signals in FL2-A vs. SSC-H plots. The CD45− cell subset was further divided into anucleate RBCs and nucleated tissue cell subsets based on signals from the Draq5 nuclear stain in FL4-A vs. SSC-H plots. The cellularity of nucleated tissue cells of interest was validated based on the signal of the cell membrane dye CellMask™ Green in FLI-A vs. FSC-H plots. Finally, live and dead tissue cells were discriminated based on 7AAD signals in FL3-A vs. SSC-H plots. All gates were established using the minced control that was digested for 60 min. Heat treated cells were used as a positive control to confirm appropriate 7AAD signals for dead cells.
Figure 18A:
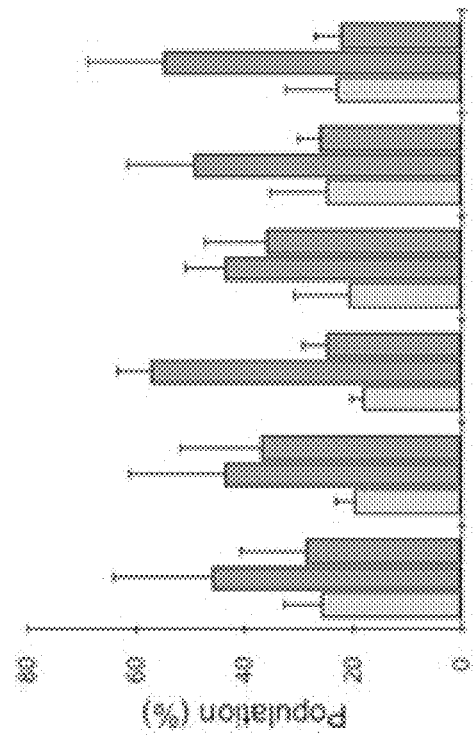
FIG. 18A illustrates flow cytometry results of mouse kidney suspensions. Flow cytometry was used to identify and quantify the number of leukocytes, red blood cells, and single tissue cells in the suspensions obtained from minced controls or device treatment. Relative numbers of each cell type are shown. Red blood cells comprised the highest percentage of almost all populations, and there was no statistically significant change in population compositions across all minced control and device conditions.
Figure 18B:
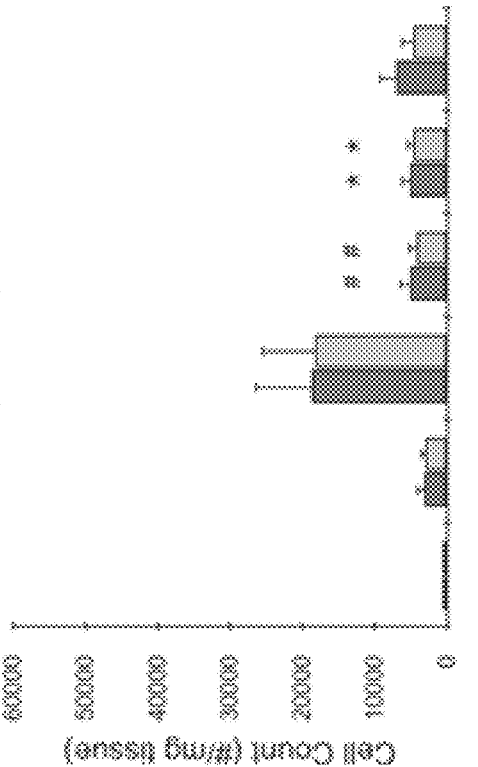
FIG. 18B illustrates flow cytometry results of mouse liver suspensions. Flow cytometry was used to identify and quantify the number of leukocytes, red blood cells, and single tissue cells in the suspensions obtained from minced controls or device treatment. Relative numbers of each cell type are shown. Red blood cells comprised the highest percentage of almost all populations, and there was no statistically significant change in population compositions across all minced control and device conditions.
Figure 18C:
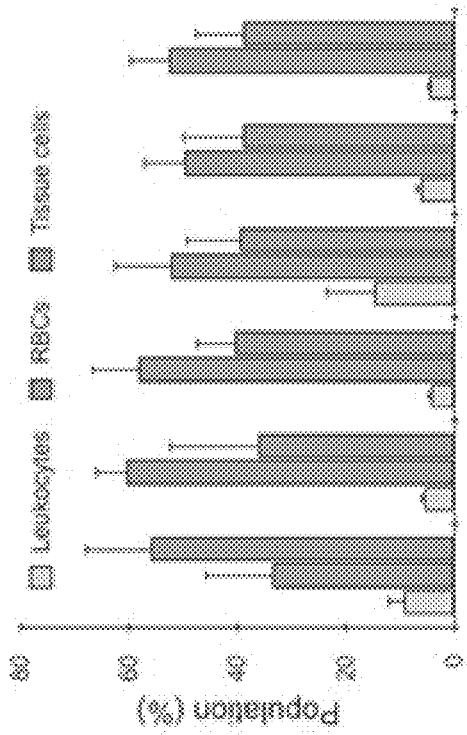
FIG. 18C illustrates a graph of total and live tissue cell numbers per mg of tissue for kidney samples.
Figure 18D:
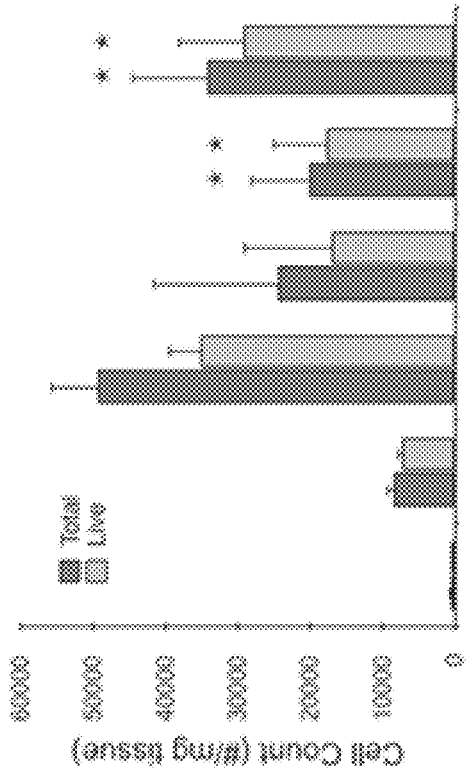
FIG. 18D illustrates a graph of total and live tissue cell numbers per mg of tissue for liver samples. For both FIGS. 18C and 18D, tissue cell recovery increased with digestion time for minced controls, but did not change significantly with device processing beyond 10 min. Importantly though, all device conditions yielded more cells than minced controls that were digested for up to 30 min. Viability remained >80% for all but the longest time points, which reached as low as 70%. The x-axis for FIGS. 18A and 18B is the same as FIGS. 18C and 18D. Error bars represent standard errors from at least three independent experiments. * indicates p<0.05 relative to minced control at the same digestion time. # indicates p<0.05 compared to minced control digested for 15 min.
Figure 19:
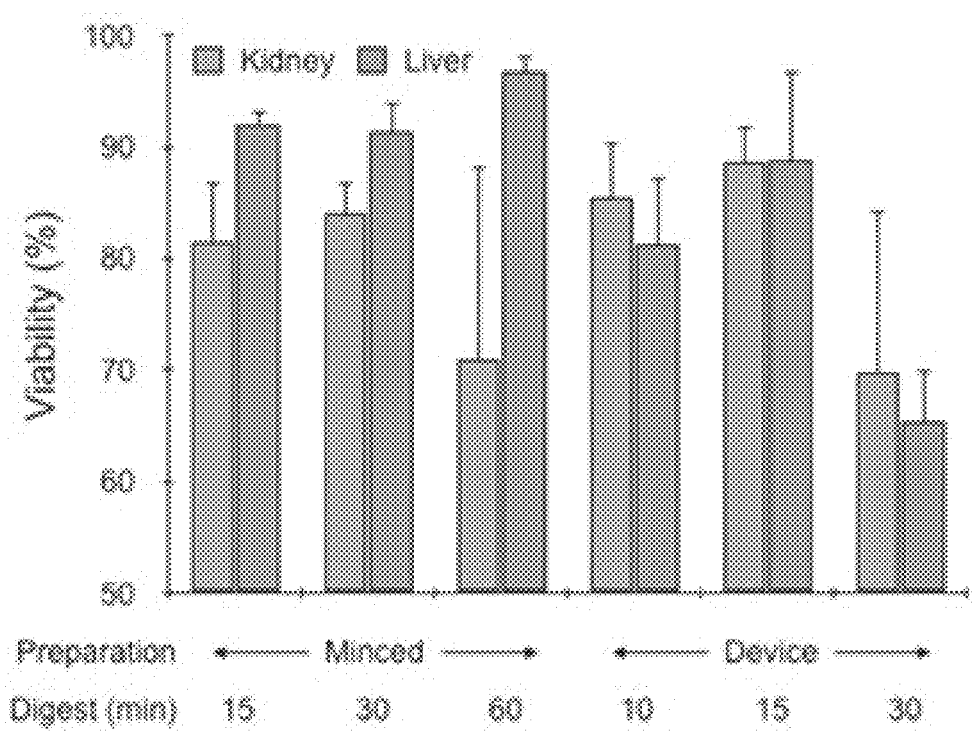
FIG. 19 illustrates a graph illustrating mouse kidney and liver cell viability data. Cell viability was similar for device treated conditions relative to minced counterparts, demonstrating minimal effect of device treatment. Error bars represent standard errors from at least three independent experiments.

This panel enabled distinction of tissue cells from non-cellular debris, anucleated red blood cells, and leukocytes, while simultaneously assessing viability. Stained cell suspensions were analyzed with a BD Accuri™ Flow Cytometer to obtain the number of each cell type using the gating protocol described in the methods section and shown in FIG. 17. Comparing the relative numbers for each cell type (FIGS. 18A and 18B), red blood cells constituted the majority of all but the minced control that was digested for 15 min. Unexpectedly, red blood cell percentage increased slightly as the tissue was digested more thoroughly, although this effect was not significant. Leukocyte percentage remained stable, decreasing slightly with digestion time. Tissue cell counts, which are expected to predominantly be epithelial, were quantified for kidney and liver samples and are presented in FIGS. 18C and 18D; respectively. Tissue cell numbers were 2 to 5 times higher for kidney than liver for the minced controls, which both increased with digestion time. The increases were more than an order of magnitude between 15 to 30 min, and 5-fold between 30 to 60 min. With device treatment, there was little change between 10 and 15 min time points, although 10 min was associated with high variability for kidney samples. Extending processing time to 30 min increased cell number by only ~50% for both tissue types, although differences were not significant. Compared to the minced controls, device treatment again provided superior results at the same digestion time point. For kidney, cell number differences were 30-fold at 15 min and 4-fold at 30 min. Differences were about half these values for liver. Furthermore, 15 min device treatment yielded similar or better results than the minced control that was digested for 30 min. However, the minced control that was digested for 60 min now provided the highest cell numbers, exceeding the 30 min device treatment by 50% for kidney and 100% for liver. This finding is in contrast to the gDNA results, particularly for kidney, but generally consistent with CyQUANT® and cell counter data. Thus, a significant portion of new cells that are liberated by the digestion device likely reside within small aggregates or clusters, which would be reasonable considering the smallest channel feature size is 200 μm. Finally, viability was assessed using a DNA dye that is excluded from healthy cells with intact membranes. Viability was approximately 80% for all kidney samples except the minced control that was digested for 60 min and 30 min device cases, which both dropped to 70% (see FIG. 19). For liver, viability was approximately 90% for the minced controls, 80% for 10 and 15 min device treatments, and 70% for 30 min device treatment. The number of live tissue cells obtained from each condition is also presented in FIGS. 18C and 18D. For kidney, 30 min device treatment produced approximately the same number of live single tissue cells as the minced control that was digested for 60 min. The 10 and 15 min device treatments produced around half of this value, but in a fraction of the time. For liver, the number of live, single tissue cells did not increase with device treatment beyond 10 min. This was likely due to the fragile nature of liver cells, which may have been damaged or fully destroyed while recirculating through the device. Overall, the microfluidic digestion device performed better for kidney samples despite the fact that this tissue type is generally considered to be more difficult to dissociate. This is likely due to the combination of kidney cells being more robust and the denser kidney tissue requiring higher shear forces to be dissociated.

A microfluidic device 10 is disclosed that is used to extract or isolate single cells from cm×mm-scale tissues using the combination of hydrodynamic shear forces and proteolytic digestion. Upon testing of the microfluidic digestion device with kidney and liver tissue samples, improvements in recovery of DNA and single tissue cells were consistently observed relative to standard methods that require mincing with a scalpel. Device performance at short processing times was particularly exciting, as a 10 min treatment yielded results that were within 50% of scalpel mincing and digesting for 1 hour, but with improved viability. Recovery improvements were most striking for DNA, suggesting that the current device design may have left a significant number of cells within small aggregates or clusters. Improvements in device function and operation may be found in improving hydro-mincing such as decreasing channel dimensions, increasing flow rate, and installing valves 54 such as illustrated in FIG. 10 to direct flow to different regions of the tissue. These approaches could also improve aggregate dissociation of tissue. In addition, the digestion device may be paired with another dissociation device 100 such as that illustrated in FIG. 2 such as the branching channel array with hydrodynamic micro-scalpels. There was some observation of evidence that cells may have been damaged during initial tissue digestion, or more likely while repeatedly recirculating through the device, particularly for liver. Thus, next generation designs will seek to remove single cells as soon as they are liberated via filtration or another means of physical separation rather than recirculation. The microfluidic device 10 may be used with other tissues such as solid tumors from various cancer types for diagnostic purposes and other healthy tissues such as skin, heart, and fat for use in tissue engineering and regenerative medicine. That is to say, various tissue types may be used in connection with the microfluidic device 10. This includes diseased tissue such as cancerous tissue or it may include healthy tissue. Moreover, the tissues or samples may be obtained from a number of different organs or tissue types.

EXAMPLE

The following is a non-limiting example of the present invention. It is to be understood that said example is not intended to limit the present invention in any way. Equivalents or substitutes are within the scope of the present invention.

Fluid Dynamics Simulations.

Flow profiles within device channels (as illustrated in FIG. 7) were simulated using COMSOL Multiphysics software. This involved coupling the Navier-Stokes equations and the continuity equation in finite element fluid dynamics simulations. Fluid flow was assumed to be laminar, and the no-slip boundary condition was enforced at the channel walls. A flow rate of 1 mL/min was used, but flow profiles remain the same at different flow rates up to 20 mL/min as used for experiments. The only difference is a corresponding change in maximum flow velocity.

Device Fabrication.

Digestion devices were designed using Onshape software. Fluidic channels and hose barb openings were laser etched using a VLS 4.60 60W $CO_2$ laser (Universal Laser Systems, Scottsdale, AZ). Channel designs were etched in 6"×6" optically clear cast acrylic sheets (McMaster-Carr, Elmhurst, IL) that served as the bottom layer of the device. Hose barb openings were then tapped to provide threading. A gasket was prepared from PDMS (Ellsworth Adhesives, Germantown, WI) by casting a 5 mm slab and cutting with a scalpel. The device was assembled with the PDMS gasket placed between the top and bottom acrylic layers, and secured with nylon screws. The inlet and outlet of the device were connected to a peristaltic pump that was controlled by a custom-built Arduino Uno R3 microcontroller.

Tissue Models.

Beef liver was purchased from a local butcher and tissue cores were extracted by using a Tru-Cut™ biopsy needle (CareFusion, Vernon Hills, IL) in a manner analogous to obtaining a clinical biopsy. Briefly, the obturator was retracted to cover the specimen notch and the cannula handle was held firmly while the needle was inserted into the tissue. The obturator was quickly advanced as far as permitted to position the specimen notch in the tissue and the cannula handle was quickly advanced to cut the tissue. Tissue obtained in the specimen notch was then transferred to device using tweezers. Mouse liver and kidneys were harvested from sacrificed C57B/6 or BALB/c mice (Jackson Laboratory, Bar Harbor, ME) that were deemed waste from a research study approved by the University of California, Irvine, Institutional Animal Care and Use Committee (courtesy of Dr. Angela G. Fleischman). Animal organs were cut with a scalpel into 1 cm long×1 mm diameter pieces, and the mass of each was recorded. Mouse kidneys were sliced in a symmetrical fashion to obtain histologically similar portions that included both cortex and medulla.

Digestion of Tissue Samples.

The digestion device was first primed with 200 μL collagenase type I (Stemcell Technologies, Vancouver, BC) and heated to 37° C. inside an incubator to ensure optimal enzymatic conditions. Tissue was then placed inside the chamber before the device was assembled, secured with nylon screws, and filled with 1 mL collagenase. Experiments were initiated by flowing fluid through the device at 20 mL/min with the peristaltic pump, and every 5 min the flow was reversed to clear tissue from the downstream sieve gates. Device effluents were collected by pumping directly into a conical tube. Controls were digested in a conical tube that contained 1 mL collagenase, either with or without prior mincing with a scalpel into ~1 mm 3 pieces. Tubes were placed inside a 37° C. incubator and gently agitated on a rotating mixer. Every 5 min, the tubes were vortexed to mechanically disrupt tissue and maximize digestion. At the conclusion of digestion procedures, all cell suspensions were repeatedly vortexed and pipetted to mechanically disrupt aggregates and treated with DNase I (10 μL; Roche, Indianapolis, IN) at 37° C. for 5 min.

Image Analysis to Monitor Tissue Digestion.

During device operation, images of the tissue were captured every 5 min using a camera mounted directly above the device as illustrated in FIG. 6. Raw images were processed using ImageJ by first converting to binary to identify the borders of the tissue (see FIG. 14). Mean gray value was then determined within the tissue border, and multiplied by the area to obtain a single metric accounting for tissue size and density. Results at each time point were normalized by the initial value prior to the experiment, and presented as percent tissue remaining.

Quantification of DNA Recovered from Cell Suspensions.

DNA content of digested cell suspensions was assessed by extraction and purification, as well as direct assessment within cells using a fluorescent DNA stain. For both cases, samples were first filtered using a 70 μm cell strainer to remove remaining tissue and large aggregates. Purified genomic DNA (gDNA) was isolated using the QIAamp® DNA Mini Kit (Qiagen, Germantown, MD) according to manufacturer's instructions and quantified using a Nanodrop ND-1000 (Thermo Fisher, Waltham, MA). DNA within cells was labelled using the CyQUANT® NF Cell Proliferation Assay Kit (Thermo Fisher, Waltham, MA) according to the manufacturer's instructions. Briefly, samples were suspended in HBSS supplemented with 35 mg/L sodium bicarbonate and 20 mM HEPES and added to an opaque 96-well plate (Corning, Corning, NY) in triplicate. An equal volume of CyQUANT® dye was then added to each well, incubated at 37° C. for 40 minutes under continuous mixing at 200 RPM, and fluorescence signal was quantified using a Synergy 2 plate reader (BioTek, Winooski, VT). Wells containing only HBSS and CyQUANT® dye were used for background subtraction. gDNA and fluorescence intensities were normalized by the initial tissue mass.

Cell Counting and Imaging of Cell Suspensions.

Digested effluents were collected, filtered using a 70 μm cell strainer, and incubated with red blood cell lysis buffer containing ammonium chloride, potassium carbonate, and EDTA (Biolegend, San Diego, CA) for 5 min at room temperature. Cell concentration was determined using a Moxi Z cell counter with type S cassettes (Orflo, Hailey, ID), and converted to cell number per mass of tissue using the total volume recovered and the initial tissue mass. Imaging was performed by transferring samples to a 12-well plate, waiting for 1 hour for the cells to settle, and capturing images using a Hoffman phase contrast microscope with a 4× objective.

Flow Cytometric Analysis of Single Cells.

Digested mouse kidney and liver cell suspensions were evenly divided into FACS tubes (Corning, Corning, NY) and resuspended in FACS Buffer (1×PBS, pH 7.4 without Ca and Mg cations) supplemented with 1% BSA and 0.1% $NaN_3$. Samples were first stained with 0.5× CellMask™ Green (Thermo Fisher, Waltham, MA) and 2.5 μg/mL anti-mouse CD45-PE monoclonal antibody (clone 30-F11, (BioLegend, San Diego, CA) for 20 minutes at 37° C. and washed twice with FACS Buffer by centrifugation. Cells were then resuspended in FACS buffer supplemented with 12.5 μM Draq5 (BioLegend, San Diego, CA) and 5 μg/mL 7AAD (BD Biosciences, San Jose, CA) and maintained on ice for at least 15 minutes prior to analysis on an Accuri Flow Cytometer (BD Biosciences). An isotype matched, PE-conjugated monoclonal antibody (clone RTK4530, BioLegend, San Diego, CA) was used as a control. Flow cytometry data was compensated and analyzed using FlowJo software (FlowJo, Ashland, OR). Compensation was determined using the kidney and liver tissues that were minced with a scalpel and digested for 60 mi, which were aliquoted into four different preparations to obtain distinct positive and negative subsets for each probe. The four preparations included cell fractions with: 1) negative control CompBeads (3.0-3.4 µm diameter, BD Biosciences, San Jose, CA) and CellMask™ Green membrane stain, 2) RBCs lysed and CD45-PE antibody, 3) live and dead (heat-killed at 55° C. for 30 min) cells with 7AAD stain, and 4) Draq5 stain. Gates encompassing the positive and negative subpopulations within each compensation sample were inputted into FlowJo to automatically calculate the compensation matrix. Finally, a sequential gating scheme was used to identify different cell subpopulations. (see FIG. 17). A SSC-A vs. FSC-A gate was created to select all cellular events and exclude debris from further analysis. Multicellular aggregates were removed from the analysis population to focus only on single cells using an FSC-H vs. FSC-A gate. Leukocytes were first distinguished from the single cell population based on CD45 expression (FL2-A or PE vs. SSC-H). Anucleate red blood cells were distinguished by their absence of Draq5 nuclear stain (FL4-A or Draq5 vs. SSC-H). The cellularity of the final remaining single cells (CD45 negative, Draq5 positive) was confirmed by detecting cell membranes using CellMask™ Green stain (FL1-A or CellMask™ green vs. FSC-H). Finally, live and dead nucleated tissue cell percentages were discriminated based on 7AAD signal (FL3-A or 7AAD vs. SSC-H).

Statistics.

Data are represented as the mean±standard error determined from at least three independent experiments. P-values were calculated using students t-test based on the mean and standard error between different experimental conditions.

While embodiments of the present invention have been shown and described, various modifications may be made without departing from the scope of the present invention. For example, aspects of one embodiment may be used in connection with other embodiments even though such substitution or combination is not explicitly described herein. Further, the publication Qiu et al., Microfluidic device for rapid digestion of tissues into cellular suspensions, Lab Chip, 17, 3300 (2017) and its supplementary information is incorporated by reference herein. Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures.

The reference numbers recited in the below claims are solely for ease of examination of this patent application, and are exemplary, and are not intended in any way to limit the scope of the claims to the particular features having the corresponding reference numbers in the drawings.

The invention, therefore, should not be limited, except to the following claims, and their equivalents.

What is claimed is:

1. A microfluidic system for the processing of a tissue sample dimensioned within the range of 1 mm$^3$ to 50 mm$^3$ into cellular suspensions comprising:
   a microfluidic device comprising:
      a substrate or chip having formed therein an inlet, an outlet, and a sample chamber dimensioned to hold the tissue sample, the sample chamber fluidically coupled at a first side to a plurality of upstream hydro-mincing microfluidic channels disposed in the substrate or chip further fluidically coupled to the inlet and coupled at a second side of the sample chamber to a plurality of downstream sieve microfluidic channels disposed in the substrate or chip further fluidically coupled to the outlet;
   wherein both the width of the upstream hydro-mincing microfluidic channels and the width of the downstream sieve microfluidic channels are greater than 50 µm and are smaller than the smallest dimension of the tissue sample.

2. The system of claim 1, wherein the width of the sample chamber is within the range of about 0.5 mm and 1 cm.

3. The system of claim 2, wherein the length of the sample chamber is less than 50 cm, and the height of the sample chamber is less than 5 cm.

4. The system of claim 3, wherein the width of the sample chamber is 2.0 mm or less, the length of the sample chamber is 2 cm or less, and the height of the sample chamber is less than 2 mm.

5. The system of claim 1, wherein the sample chamber is closed to an external environment by a removable plug.

6. The system of claim 1, wherein the sample chamber comprises a septum located on a side of the substrate or chip.

7. The system of claim 1, wherein the upstream hydro-mincing microfluidic channels have a width with the range of about 100 µm to about 200 µm.

8. The system of claim 1, wherein the downstream sieve microfluidic channels have a width within the range of about 10 µm to about 1 mm.

9. The system of claim 1, wherein the downstream sieve microfluidic channels have a width within the range of about 500 µm to about 1 mm.

10. The system of claim 1, wherein the number of sieve microfluidic channels is equal to the number of upstream hydro-mincing microfluidic channels.

11. The system of claim 1, further comprising a pump configured to pump a fluid containing a digestive enzyme into the inlet.

12. The system of claim 11, wherein the fluid comprises recirculated fluid obtained from the microfluidic device.

13. The system of claim 12, wherein the outlet is fluidly connected to a junction, wherein the junction is fluidically connected to an exit tube and a recirculation tube, wherein the recirculation tube is fluidly connected to the inlet, and wherein the tissue sample is directed through the exit tube and the fluid is directed through the recirculation tube.

14. The system of claim 1, further comprising a plurality of valves located within the plurality of hydro-mincing microfluidic channels, the plurality of valves configured to turn on/off individual hydro-mincing microfluidic channels.

15. The system of claim 1, further comprising a secondary tissue dissociation device coupled to an outlet of the microfluidic device.

16. The system of claim 1, further comprising a loading port connected to the sample chamber by a via.

17. The system of claim 1, wherein the substrate or chip comprises multiple layers sandwiched together.

18. The system of claim 17, wherein the sample chamber is disposed in one layer and an inlet channel and an outlet channel that are fluidically coupled to the sample chamber are each located in a separate layer.

19. The system of claim 18, wherein the sample chamber is disposed in a surface layer and further comprises a cap or lid for sealing the sample chamber from an external environment of the microfluidic device.

20. The system of claim 1, wherein a first instance of the microfluidic device is capable of being coupled to at most two additional instances of the microfluidic device, wherein the coupling occurs at a third side of the sample chamber, a fourth side of the sample chamber, or a combination thereof.

21. A method of processing tissue in a microfluidic device comprising a substrate or chip having formed therein an inlet, an outlet, and a sample chamber dimensioned to hold the tissue sample, the sample chamber fluidically coupled at one side to a plurality of upstream hydro-mincing microfluidic channels disposed in the substrate or chip and further fluidically coupled to the inlet and coupled at another side of the sample chamber to a plurality of downstream sieve microfluidic channels disposed in the substrate or chip and further fluidically coupled to the outlet, the method comprising:
- placing the tissue within the sample chamber; and
- flowing a fluid containing a digestive enzyme into the inlet.

22. The method of processing tissue according to claim 21, further comprising capturing fluid exiting the outlet and recirculating the captured fluid into the inlet.

* * * * *